United States Patent
Segura et al.

(10) Patent No.: US 9,505,867 B2
(45) Date of Patent: Nov. 29, 2016

(54) TRIBLOCK COPOLYMERS FOR CYTOPLASMIC DELIVERY OF GENE-BASED DRUGS

(75) Inventors: Tatiana Segura, Los Angeles, CA (US); Jeffrey A. Hubbell, Lausanne (CH)

(73) Assignee: Ecole Polytechmique Fédérale De Lausanne, Lausanne (CH)

( * ) Notice: Subject to any disclaimer, the term of this patent is extended or adjusted under 35 U.S.C. 154(b) by 1540 days.

(21) Appl. No.: 11/916,252

(22) PCT Filed: May 31, 2006

(86) PCT No.: PCT/US2006/020760
§ 371 (c)(1),
(2), (4) Date: May 21, 2010

(87) PCT Pub. No.: WO2007/008300
PCT Pub. Date: Jan. 18, 2007

(65) Prior Publication Data
US 2010/0222407 A1    Sep. 2, 2010

Related U.S. Application Data

(60) Provisional application No. 61/686,188, filed on May 31, 2005.

(51) Int. Cl.
*A61L 31/04* (2006.01)
*C08F 297/02* (2006.01)
*C08L 53/00* (2006.01)

(52) U.S. Cl.
CPC ............ *C08F 297/02* (2013.01); *A61L 31/048* (2013.01); *C08L 53/00* (2013.01); *C08L 53/005* (2013.01)

(58) Field of Classification Search
None
See application file for complete search history.

(56) References Cited

U.S. PATENT DOCUMENTS

| | | |
|---|---|---|
| 4,242,474 A | 12/1980 | Shinohara et al. |
| 4,618,400 A | 10/1986 | Wood et al. |
| 4,732,938 A | 3/1988 | Grant et al. |
| 4,923,924 A | 5/1990 | Grant et al. |
| 5,268,305 A | 12/1993 | Ribi et al. |
| 5,294,690 A | 3/1994 | Iguchi et al. |
| 5,330,911 A | 7/1994 | Hubbell et al. |
| 5,374,668 A | 12/1994 | Kanemura et al. |
| 5,410,016 A | 4/1995 | Hubbell et al. |
| 5,427,915 A | 6/1995 | Ribi et al. |
| 5,446,090 A | 8/1995 | Harris |
| 5,502,102 A | 3/1996 | Nazareth |
| 5,529,914 A | 6/1996 | Hubbell et al. |
| 5,567,422 A | 10/1996 | Greenwald |
| 5,573,934 A | 11/1996 | Hubbell et al. |
| 5,575,815 A | 11/1996 | Slepian et al. |
| 5,612,390 A | 3/1997 | Iguchi et al. |
| 5,635,207 A | 6/1997 | Grinstaff et al. |
| 5,648,506 A | 7/1997 | Desai et al. |
| 5,702,717 A | 12/1997 | Cha et al. |
| 5,752,974 A | 5/1998 | Rhee et al. |
| 5,801,033 A | 9/1998 | Hubbell et al. |
| 5,817,840 A | 10/1998 | Nicolaou et al. |
| 5,852,182 A | 12/1998 | Cook et al. |
| 5,858,746 A | 1/1999 | Hubbell et al. |
| 5,874,500 A | 2/1999 | Rhee et al. |
| 5,880,131 A | 3/1999 | Greenwald et al. |
| 5,897,955 A | 4/1999 | Drumheller |
| 5,932,462 A | 8/1999 | Harris et al. |
| 5,945,457 A | 8/1999 | Plate et al. |
| 5,965,588 A | 10/1999 | Vazquez et al. |
| 6,180,141 B1 | 1/2001 | Lemercier et al. |
| 6,224,903 B1 | 5/2001 | Martin et al. |
| 6,624,245 B2 * | 9/2003 | Wallace et al. ............ 525/54.1 |
| 7,056,704 B2 * | 6/2006 | Tuschl et al. ............. 435/91.1 |
| 7,132,475 B2 | 11/2006 | Hubbell et al. |
| 9,271,929 B2 | 3/2016 | Dixon et al. |
| 2003/0044468 A1 | 3/2003 | Cellesi et al. |
| 2003/0059906 A1 * | 3/2003 | Hubbell et al. ............ 435/135 |
| 2003/0133963 A1 | 7/2003 | Hubbell et al. |
| 2003/0134420 A1 * | 7/2003 | Lollo et al. ............... 435/455 |

(Continued)

FOREIGN PATENT DOCUMENTS

| | | |
|---|---|---|
| FR | 2809617 | 12/2001 |
| GB | 1203577 | 8/1970 |

(Continued)

OTHER PUBLICATIONS

Benoit et al (Molecular Pharmaceutics vol. 7, No. 2, 442-455, 2010).*
Ryter et al (EMBO J. 17(24): 7505-7513, 1998).*
NCBI Accession NP_001079500 (2012).*
Sowter et al (Cancer Research 63, 6130-6134, Oct. 1, 2003).*
Saito et al (Gene Therapy (2003) 10, 72-83).*
Walker et al (Molecular Therapy vol. 11, No. 3, Mar. 2005, available Dec. 18, 2004).*
Notice of Reasons for Rejection for Japanese Patent Application No. 2008-514756 dated May 23, 2012 (and English translation).
Aida et al., "Zinc N-substituted Porphyrins as Novel Initiators for the Living and Immortal Polymerizations of Episulfide," *Macromolecules* 23: 3887-3892, 1990.

(Continued)

*Primary Examiner* — Richard Schnizer
(74) *Attorney, Agent, or Firm* — Clark & Elbing LLP

(57) ABSTRACT

The invention features a triblock copolymer including a hydrophilic block; a hydrophobic block; and a positively charged block capable of reversibly complexing a negatively charged molecule, e.g., a nucleic acid, wherein the hydrophobic block is disposed between the hydrophilic block and the positively charged block. Desirably, the triblock copolymer is capable of self-assembling into a supramolecular structure, such as a micelle or vesicle. The invention further features methods of delivering negatively charged molecules and methods of treating a disease or condition using the polymers of the invention.

36 Claims, 11 Drawing Sheets

(56) References Cited

U.S. PATENT DOCUMENTS

| | | | |
|---|---|---|---|
| 2003/0153001 A1 | 8/2003 | Soane et al. | |
| 2003/0166601 A1* | 9/2003 | Woodle et al. | 514/44 |
| 2003/0215588 A1 | 11/2003 | Yeager et al. | |
| 2005/0169899 A1* | 8/2005 | Diamond | 424/93.21 |
| 2006/0057215 A1 | 3/2006 | Raiche et al. | |
| 2006/0057222 A1 | 3/2006 | Linhardt et al. | |
| 2006/0224095 A1* | 10/2006 | Claverie et al. | 602/5 |
| 2007/0287672 A1* | 12/2007 | Creighton | A61K 31/10 424/70.11 |
| 2008/0097087 A1* | 4/2008 | Nagasaki et al. | 536/22.1 |

FOREIGN PATENT DOCUMENTS

| | | |
|---|---|---|
| GB | 1348045 | 3/1974 |
| JP | 2000-507934 | 6/2000 |
| JP | 2001-504093 | 3/2001 |
| JP | 2003-500504 | 1/2003 |
| JP | 2004-517979 | 6/2004 |
| JP | 2005-522552 | 7/2005 |
| JP | 2005-298542 | 10/2005 |
| JP | 2006-506335 | 2/2006 |
| JP | 2007-522274 | 8/2007 |
| JP | 2008-534732 A | 8/2008 |
| WO | WO 95/13312 | 5/1995 |
| WO | WO 97/15287 | 5/1997 |
| WO | WO 97/22371 | 6/1997 |
| WO | WO 98/16202 | 4/1998 |
| WO | WO 98/32466 | 7/1998 |
| WO | WO 99/14259 | 3/1999 |
| WO | WO 99/22770 | 5/1999 |
| WO | WO 99/34833 | 7/1999 |
| WO | WO 00/09087 | 2/2000 |
| WO | WO 00/44808 | 8/2000 |
| WO | WO 00/71606 | 11/2000 |
| WO | WO 01/02017 | 1/2001 |
| WO | WO 01/92584 | 12/2001 |
| WO | WO 01/93820 | 12/2001 |
| WO | WO 02/055185 | 7/2002 |
| WO | WO 03/087223 | 10/2003 |
| WO | WO 2004/009664 | 1/2004 |
| WO | WO 2005/068533 | 7/2005 |
| WO | WO 2006/107311 | 10/2006 |
| WO | WO 2006/109945 A1 | 10/2006 |
| WO | WO 2006/137855 | 12/2006 |
| WO | WO 2006/137856 | 12/2006 |
| WO | WO 2010/068432 | 6/2010 |

OTHER PUBLICATIONS

Baker, *Controlled Release of Biologically Active Agents* Bruck, ed., pp. 84-131 John Wiley and Sons, New York, 1987.

Ballini et al., "Amberlyst A-27, an Efficient Heterogeneous Catalyst for the Michael Reactions of Nitroalkanes with β-substituted Alkene Acceptors," *J. Org. Chem.* 61: 3209-3211, 1996.

Bell et al., "Transfection Mediated by Gemini Surfactants: Engineered Escape from the Endosomal Compartment," *J. Am. Chem. Soc.* 125: 1551-1558, 2003.

Bertrand et al., "Comparison of Antisense Oligonucleotides and siRNAs in Cell Culture and In Vivo," *Biochem. Biophys. Res. Commun.* 296: 1000-1004, 2002.

Blessing et al., "Different Strategies for Formation of PEGylated EGF-Conjugated PEI/DNA Complexes for Targeted Gene Delivery," *Bioconjug. Chem.* 12: 529-537, 2001.

Blume et al., "Specific Targeting with Poly(ethylene glycol)-modified Liposomes: Coupling of Homing Devices to the Ends of the Polymeric Chains Combines Effective Target Binding with Long Circulation Times," *Biochim. Biophys. Acta* 1149: 180-184, 1993.

Booth et al., "Effects of Block Architecture and Composition on the Association Properties of Poly(oxyalkylene) Copolymers in Aqueous Solution," *Macromol. Chem. Rapid Commun.* 21: 501-527, 2000.

Boyland et al., "Enzymes Catalysing Conjugations of Glutathione with Alpha-beta-unsaturated Carbonyl Compounds," *Biochem. J.* 109: 651-661, 1968.

Carlisle, "Use of Adenovirus Proteins to Enhance the Transfection Activity of Synthetic Gene Delivery Systems," *Curr. Opin. Mol. Ther.* 4: 306-312, 2002.

Chandaroy et al., "Utilizing Temperature-sensitive Association of Pluronic F-127 with Lipid Bilayers to Control Liposome-cell Adhesion," *Biochim. Biophys. Acta* 1559: 32-42, 2002.

Chasseaud, "Distribution of Enzymes that Catalyse Reactions of Glutathione with Alpha Beta-unsaturated Compounds," *Biochem. J.* 131: 765-769, 1973.

Czauderna et al., "Structural Variations and Stabilising Modifications of Synthetic siRNAs in Mammalian Cells," *Nucleic Acids Res.* 31: 2705-2716, 2003.

Deutsch et al., "Synthesis of Congeners and Prodrugs. 3. Water-soluble Prodrugs of Taxol with Potent Antitumor Activity," *J. Med. Chem.* 32: 788-792, 1989.

Discher et al., "Polymersomes: Tough Vesicles Made from Diblock Copolymers," *Science* 284: 1143-1146, 1999.

Dumitriu et al., "Polymeric Drug Carriers," in *Polymeric Biomaterials*, Dumitriu, ed., pp. 435-449 and 466-724, Marcel Dekker, New York, 1994.

Duncan et al., "Soluble Synthetic Polymers as Potential Drug Carriers," *Adv. in Polym. Sci.* 57: 51-101, 1984.

East et al., "The Mannose Receptor Family," *Biochim. Biophys. Acta* 1572: 364-386, 2002.

Eisele et al., "Kinetics of Photocrosslinking Reactions of a DCPA/EA Matrix in the Presence of Thiols and Acrylates," *J. Polym. Sci.* 35: 2333-2345, 1997.

Elbashir et al., "Duplexes of 21-Nucleotide RNAs Mediate RNA Interference in Cultured Mammalian Cells," *Nature* 411: 494-498, 2001.

Erbacher et al., "Gene Transfer by DNA/Glycosylated Polylysine Complexes into Human Blood Monocyte-Derived Macrophages," *Hum. Gene Ther.* 7: 721-729, 1996.

Fan et al., "Molecular Recognition and Catalysis: Incorporation of an "Oxyanion Hole" into a Synthetic Receptor," *New J. Chem.* 21: 81-85, 1997.

Frankel et al., "Cellular Uptake of the Tat Protein from Human Immunodeficiency Virus," *Cell* 55: 1189-1193, 1988.

Friedman et al., "Relative Nucleophilic Reactivities of Amino Groups and Mercaptide Ions in Addition Reactions with α,β-Unsaturated Compounds," *J. Am. Chem. Soc.* 87: 3672-3682, 1965.

Gabizon et al., "Targeting Folate Receptor with Folate Linked to Extremities of Poly(ethylene glycol)-grafted Liposomes: In Vitro Studies," *Bioconjugate Chem.* 10: 289-298, 1999.

Ghandehari et al., "In Vitro Degradation of pH-sensitive Hydrogels Containing Aromatic Azo Bonds," *Biomaterials* 18: 861-872, 1997.

Gottschalk et al., "Folate Receptor Mediated DNA Delivery into Tumor Cells: Potosomal Disruption Results in Enhanced Gene Expression," *Gene Ther.* 1: 185-191, 1994.

Green et al., "Autonomous Functional Domains of Chemically Synthesized Human Immunodeficiency Virus Tat Trans-activator Protein," *Cell* 55: 1179-1188, 1988.

Greenwald et al., "Drug Delivery Systems: Water Soluble Taxol-2'-Poly(ethylene glycol) Ester Prodrugs-design and In Vivo Effectiveness," *J. Med. Chem.* 39: 424-431, 1996.

Greenwald et al., "Camptothecin-20-PEG Ester Transport Forms: the Effect of Spacer Groups on Antitumor Activity," *Bioorg. Med. Chem.* 6: 551-562, 1998.

Grünweller et al., "Comparison of Different Antisense Strategies in Mammalian Cells Using Locked Nucleic Acids, 2'-O-Methyl RNA, Phosphorothioates and Small Interfering RNA," *Nucleic Acids Res.* 31: 3185-3193, 2003.

Harbottle et al., "An RGD-oligolysine Peptide: a Prototype Construct for Integrin-mediated Gene Delivery," *Hum. Gene Ther.* 9: 1037-1047, 1998.

Hern et al., "Incorporation of Adhesion Peptides into Non-adhesive Hydrogels Useful for Tissue Resurfacing," *J. Biomed. Mater. Res.* 39: 266-276, 1998.

Hirai et al., "Ph-induced Structure Change of Poly(vinyl alcohol) Hydrogel Crosslinked with Poly(acrylic acid)," *Die Angewandte Makromolekulare Chemie* 240: 213-219, 1996.

(56) References Cited

OTHER PUBLICATIONS

Inoue et al., "Gene Therapy of Human Bladder Cancer with Adenovirus-mediated Antisense Basic Fibroblast Growth Factor," *Clinical Cancer Research* 6: 4422-4431, 2000.
Ishihara et al., "Tris(pentafluorphenyl)boron as an Efficient, Air Stable, and Water Tolerant Lewis Acid Catalyst," *Bull. Chem. Soc. Jpn.* 68: 1721-1730, 1995.
Jousma et al., "Characterization of Liposomes. The Influence of Extrusion of Multilamellar Vesicles Through Polycarbonate Membranes on Particle Size, Particle Size Distribution and Number of Bilayers," *Int. J. Pharm.* 35: 263-274, 1987.
Kabanov et al., "Pluronic® Block Copolymers as Novel Polymer Therapeutics for Drug and Gene Delivery," *J. Control Release* 82: 189-212, 2002.
Katayose et al., "Water-soluble Polyion Complex Associates of DNA and Poly(ethylene glycol)-poly(L-lysine) Block Copolymer," *Bioconjug. Chem.* 8: 702-707, 1997.
Kawai et al., "New Application of Solid Acid to Carbon-Carbon Bond Formation Reactions: Clay Montmorillonite-catalyzed Aldol Reactions of Silyl Enol Ethers with Aldehydes and Acetals," *Bull. Chem. Soc. Jpn.* 61: 1237-1245, 1988.
Kircheis et al., "Coupling of Cell-Binding Ligands to Polyethylenimine for Targeted Gene Delivery," *Gene Ther.* 4: 409-418, 1997.
Kito et al., "Biocompatible Coatings for Luminal and Outer Surfaces of Small-caliber Artificial Grafts," *Journal of Biomedical Materials Research* 30: 321-330, 1996.
Kopecek et al., "Controlled Release of Drug Model from N-(2-hydroxypropyl)-methacrylamide Copolymers," *Ann. N.Y. Acad. Sci.* 446: 93-104, 1985.
Lasic et al., *Stealth Liposomes*, Chapters 2, 4, and 9, CRC Press: Boca Raton, FL, 1995.
Lau et al., "Conjugation of Doxorubicin to Monoclonal Anti-Carcinoembryonic Antigen Antibody via Novel Thiol-directed Cross-linking Reagents," *Bioorg. Med. Chem.* 3: 1299-1304, 1995.
Lau et al., "Novel Doxorubicin-monoclonal Anti-carcinoembryonic Antigen Antibody Immunoconjugate Activity In Vitro," *Bioorg. Med. Chem.* 3: 1305-1312, 1995.
Mathur et al., "Methods for Synthesis of Hydrogel Networks: A Review," *J.M.S—Rev. Macromol. Chem. Phys.* C36: 405-430, 1996.
McCaffrey et al., "RNA Interference in Adult Mice," *Nature* 418: 38-39, 2002.
Moghaddam et al., "Molecular Design of Three-dimensional Artificial Extracellular-matrix Photosensitive Polymers Containing Cell Adhesive Peptide," *J. Polymer Sci.* 51: 1589-1597, 1993.
Morpurgo et al., "Preparation and Characterization of Poly(ethylene glycol) Vinyl Sulfone," *Bioconjug. Chem.* 7: 363-368, 1996.
Mortensen, "Block Copolymer in Aqueous Solution: Micelle Formation and Hard-Sphere Crystallization," *Prog. Colloid. Polym. Sci.* 93: 72-75, 1993.
Napoli et al., "New Synthetic Methodologies for Amphiphilic Multiblock Copolymers of Ethylene Glycol and Propylene Sulfide," *Macromolecules* 34: 8913-8917, 2001.
Napoli et al., "Lyotropic Behavior in Water of Amphiphilic ABA Triblock Copolymers Based on Poly(Propylene Sulfide) and Poly(Ethylene Glycol)," *Langmuir* 18: 8324-8329, 2002.
Napoli et al., "Oxidation-Responsive Polymeric Vesicles," *Nat. Mater.* 3: 183-189, 2004.
Pathak et al., "Rapid Photopolymerization of Immunoprotective Gels in Contact with Cells and Tissue," *J. Am. Chem. Soc.* 114: 8311-8312, 1992.
Pató et al., "Polymers Containing Enzymatically Degradable Bonds, 9a) Chymotrypsin Catalyzed Hydrolysis of a p-nitroanilide Drug Model, Bound via Oligopeptides onto Poly(vinylpyrrolidone-co-maleic anhydride)," *Makromol. Chem.* 185: 231-237, 1984.

Pendri et al. "Antitumor Activity of Paclitaxel-2'-glycinate Conjugated to Poly(ethylene glycol): a Water-soluble Prodrug," *Anticancer Drug Des.* 13: 387-395, 1998.
Petka et al., "Reversible Hydrogels from Self-assembling Artificial Proteins," *Science* 281: 389-392, 1998.
Pitt et al., "Controlled Drug Delivery," in *Biodegradation of Polymers, Basic Concepts*, vol. 1, pp. 53-80, CRC Press, Boca Raton, Florida, 1983.
Reich et al., "Small Interfering RNA (siRNA) Targeting VEGF Effectively Inhibits Ocular Neovascularization in a Mouse Model," *Mol. Vis.* 9: 210-216, 2003.
Romanowska et al., "Michael Additions for Syntheses of Neoglycoproteins," *Methods in Enzymol.* 242: 90-101, 1994.
Sawhney et al., "Bioerodible Hydrogels Based on Photopolymerized Poly(ethylene glycol)-co-Poly($\alpha$-hydroxy acid) Diacrylate Macromers," *Macromolecules* 26: 581-587, 1993.
Simeoni et al., "Insight into the Mechanism of the Peptide-Based Gene Delivery System MPG: Implications for Delivery of siRNA into Mammalian Cells," *Nucleic Acids Res.* 31: 2717-2724, 2003.
Tanaka et al., "Michael-type Addition of Illudin S, a Toxic Substance from Lampteromyces japonicus, with Cysteine and Cysteine-Containing Peptides In Vitro, " *Chem. Pharm. Bull.* 44: 273-279, 1996.
Torchilin et al., "Poly(ethylene glycol) on the Liposome Surface: on the Mechanism of Polymer-coated Liposome Longevity," *Biochim. Biophys. Acta* 1195: 11-20, 1994.
Watanabe et al., "First Example of Photoinduced Copolymerizability Enhancement. Copolymerization of Epoxide and Episulfide Initiated with Zinc N-substituted Porphyrin under Visible Light Irradiation," *Macromolecules* 24: 3970-3972, 1991.
West et al., "Comparison of Covalently and Physically Cross-linked Polyethylene Glycol-based Hydrogels for the Prevention of Postoperative Adhesions in a Rat Model," *Biomaterials* 16: 1153-1156, 1995.
Won et al., "Giant Wormlike Rubber Micelles," *Science* 283: 960-963, 1999.
Wright et al., *The Chemistry and Pharmacology of Taxol and Its Derivatives*, Farina, ed., pp. 110-130 and 165-300, Elsevier, New York, 1995.
Yu et al., "Bilayer Morphologies of Self-assembled Crew-cut Aggregates of Amphiphilic PS-b-PEO Diblock Copolymers in Solution," *Macromolecules* 31: 3509-3518, 1998.
Zalipsky et al., "Attachment of Drugs to Polyethylene Glycols," *Eur. Polym. J.* 19: 1177-1183, 1983.
Zalipsky et al., "Peptide Attachment to Extremities of Liposomal Surface Grafted PEG Chains: Preparation of the Long-circulating Form of Laminin Pentapeptide, YIGSR," *Bioconjugate Chem.* 6: 705-708, 1995.
Zalipsky, "Long-circulating, Polyethylene Glycol-grafted Immunoliposomes," *J. Control. Release* 39: 153-161, 1996.
Zhao et al., "Novel Degradable PEG Esters for Drug Delivery: Synthesis and Characterization," *Polymer Reprints* 38: 526-527, 1997.
Zhou et al., "Self-Assembly in a Mixture of Two Poly(Ethylene Oxide)-b-Poly(Propylene Oxide)-b-Poly(Ethylene Oxide) Copolymers in Water," *J. Colloid Interface Sci.* 183: 339-350, 1996.
International Preliminary Report on Patentability for International Application No. PCT/US06/20760, dated Dec. 6, 2007.
International Search Report for International Application No. PCT/US06/20760, dated Mar. 21, 2007.
Extended European Search Report for Application No. 10013466.7-2102, dated Feb. 17, 2011.
Extended European Search Report for Application No. 06799931.8-2102, dated May 30, 2008.
Segura et al., "Synthesis and in vitro characterization of an ABC triblock copolymer for siRNA delivery," *Bioconjug Chem.* 18(3):736-45 (2007).

\* cited by examiner

| Compound | Type | Assignment | ppm | r |
|---|---|---|---|---|
| PEG-allyl | m | Allyl | 5.8 | 1 |
|  | s | PEG | 3.6 | 1.74 |
| PEG-thioacetate | s | Thiocetate | 2.4 | 55.3 |
|  | s | PEG | 3.6 | 3281 |
| PEG-PPS$_5$-py | s | PPS | 1.4 | 23.66 |
|  | s | PEG | 3.6 | 283.3 |
|  | m | pyridine | 7.6 | 1.34 |
| PEG-PPS$_{10}$-Py | s | PPS | 1.4 | 55.3 |
|  | s | PEG | 3.6 | 274.6 |
|  | m | pyridine | 7.6 | 1.17 |

|  | Mn | Mw | PD |
|---|---|---|---|
| PEG-PPS$_5$-py | 3077.8 | 2682.53 | 1.147 |
| PEG-PPS$_{10}$-py | 4149.1 | 3294.43 | 1.259 |

Figure 4

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Arg Lys Lys Arg Arg Gln Arg Arg
1               5

<210> SEQ ID NO 2
<211> LENGTH: 13
<212> TYPE: PRT
<213> ORGANISM: Artificial Sequence
<220> FEATURE:
<223> OTHER INFORMATION: Synthetic Construct

<400> SEQUENCE: 2

Cys Gly Gly Trp Arg Lys Lys Arg Arg Gln Arg Arg Arg
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Cys Gly Gly Trp Lys Lys Lys Lys Lys Lys Lys Lys Lys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct

<400> SEQUENCE: 4
```

```
Lys Lys Lys Lys Lys Lys Lys Lys Lys
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Arg Arg Arg Arg Arg Arg Arg Arg Arg
1               5
```

TRIBLOCK COPOLYMERS FOR CYTOPLASMIC DELIVERY OF GENE-BASED DRUGS

BACKGROUND OF THE INVENTION

The invention relates to the fields of polymer chemistry and nucleic acid transfection.

There are currently two methods used to silence the expression of a target gene: antisense oligonucleotides (ODN) and RNA interference (RNAi). Until recently, ODNs had been the main hope for decreasing or silencing gene expression for therapeutic purposes. ODNs are short pieces of DNA or RNA complementary to messenger RNA (mRNA) sequences. They function by hybridizing with the mRNA to create a double stranded region. In the case of DNA ODNs, a RNA-DNA duplex is formed, which can be recognized by an RNAse, thus degrading the mRNA and eliminating protein expression by the targeted sequence. This process has been successful in vitro, but the lack of an appropriate delivery mechanism has limited in vivo applications [9]. The second method of gene silencing is RNAi, first described in worms in 1998 [3]. It was later found that this phenomenon also operates in insects [4], frogs [5], mice [6], and it is now believed to exist in all animals. The natural function of RNAi appears to be protection of the genome against invasion by mobile genetic material elements such as transposons and viruses. Transposons and viruses produce aberrant RNA or dsRNA when they become active [7], and it is, thus, desirable to eliminate such nucleic acids. Once this dsRNA (>30 nucleotides (nt)) is inside the cell, the process of RNAi begins with the enzymatic degradation of the dsRNA into roughly 22 nucleotide-long dsRNA segments, termed small interfering RNA (siRNA) [8]. The siRNA along with nucleases and other proteins assemble into the RNA induced silencing complex (RISC). The RISC enables the antisense strand of the siRNA to bind to the complementary sequence of mRNA, and, this bound complex, in turn, induces the degradation of the complementary mRNA. In mammalian cells, if the process is initiated by long dsRNA (>30 nt), the interferon response is activated and protein kinase R and RNAse I are activated leading to the arrest of all protein synthesis. Apoptosis of the cell following delivery of siRNA (<30 nt) has been shown to be an efficient way of silencing a specific gene without compromising gene expression, more generally, in mammalian cells. The structure of siRNA typically consists of 21-22 nucleotide double stranded RNA (dsRNA) with 2-3 nucleotide long 3' overhangs [10]. Silencing genes via siRNA is a highly efficient process, reported to be 1000-fold more effective than ODNs [9]. The delivery of siRNA for biomedical applications is very promising because of its stringent sequence-specific action. A single base mismatch over the length of the siRNA is enough to prevent induction of the response [10].

The ability to down-regulate gene expression specifically using the RNAi pathway or antisense oligonucleotides and to up-regulate gene expression via non-viral gene delivery has tremendous potential as a therapeutic and as a tool in basic science. However, an efficient delivery system capable of specifically delivering small interfering RNA (siRNA), antisense oligonucleotides (ODN), or plasmid DNA (pDNA) to target cells is currently unavailable. Cationic polymers that can self assemble with nucleic acids based on charge are some of the most widely studied and commonly utilized gene delivery vehicles. Limitations of cationic-based gene delivery systems include toxicity, aggregation, and unpacking of the DNA. siRNA delivery suffers from many of the same limitations as non-viral gene delivery approaches, including targeted internalization and endosomal escape, for which a delivery system is yet to be found that is as efficient as viral vectors. Following receptor-mediated uptake into coated pits and endocytosis, the endosomes are shuttled toward lysosomal fusion, with degradation of their contents. Only a small fraction of the endosomal contents escape.

siRNA has been shown to be functional in vitro and in vivo, mediating targeted gene silencing in a variety of models. Reporter genes have been extensively utilized as proof of principle for siRNA delivery both in in vitro systems [9, 13] and in adult mice [1, 21]. The silencing of therapeutically relevant genes has also shown some success in the inhibition of neovascularization by delivering siRNA targeting for VEGF [21].

Silencing of genes using siRNA requires that the siRNA be internalized by the cell and transferred to the cytosol where the RNAi pathway is activated, the targeted mRNA destroyed, and the gene of interest silenced. siRNA delivery suffers from many of the same limitations as other non-viral gene delivery approaches such as targeted internalization and endosomal escape, for which a delivery system is yet to be found that is as efficient as viral vectors. Nevertheless current strategies for the delivery of siRNA employ the same delivery vectors as used for non-viral gene delivery such as cationic polymers, lipids [11, 12], and peptides [13], which self assemble with siRNA electrostatically. Two key differences in the mechanism of action of siRNA and plasmids are that siRNA does not need to cross the nuclear barrier to be active and that siRNA is much smaller in size with the possibility of chemical modifications without loss of activity [11]. The fact that siRNA does not need to enter the nucleus is a marked advantage since efficient delivery of DNA to cells requires actively dividing cells where the nuclear membrane is compromised or with vectors that contain nuclear localization sequences. Furthermore, since siRNA is double stranded, it is less susceptible to degradation than other RNA silencing approaches making it a more robust material for chemical modification and delivery. The cationic polymer delivery system for plasmid DNA has been extensively modified with functional domains to design a synthetic vector capable of overcoming the barriers to gene transfer and may be applied to siRNA delivery.

The ability to silence any gene in the genome can be used to augment healthy tissue formation and wound healing by down regulating key molecules, which when expressed, suppress instead of induce tissue formation or regeneration. For example, after abdominopelvic surgery, the accumulation of fibrin between adjacent sides of the wound prevents the regeneration of healthy functional tissue. Abdominal surgery near organs, such as fallopian tubes or the small intestine, poses particular problems since adhesions can constrict the tubes and cause infertility [2, 3], In 1994, adhesions occurred in 90 percent of the 3.1 million US patients undergoing abdominal surgery, with approximately 15 percent undergoing secondary procedures to remove adhesions [4]. Although barriers and polymer lavages have been introduced, the problem remains largely unsuccessfully treated. As to mechanism, postoperative adhesion formation has been associated with a decreased capacity of the mesothelial cells to degrade intra-abdominal deposited fibrin as a result of inhibition of plasminogen activator activity (PAA) by PAI-1 [5]. PAI-1 activity is regulated in part by HIF-1α, a transcription factor, which is, in turn, upregulated by hypoxia in the site of injury [6]. Therefore, targeting the mRNAs of PAI-1 and HIF-1α could be used to tip the balance between fibrin formation and fibrin resorption toward overall resorption, thus preventing abdominal adhesions. HIF-1α regulates the production of a number of other scar-forming proteins, including transforming growth factor β (TGFβ), and, as such, inhibition of the transcription factor may have multiple positive effects. It is also noteworthy that it has been previously been found that treatment of surgical subjects with tissue plasminogen activator and ancrod [7,8] did not inhibit favorable healing, demonstrating that the coagulation/fibrinolysis balance within the tissue is more robust than in the peritoneal cavity. Given that PAI-1 and HIF-1α are produced by mesothelial cells on the surface of the peritoneum and fibroblast invading the fibrin coagulum at the site of injury, multiple cellular targets are present to which to deliver such therapeutics.

Thus, there is a need for new delivery systems for nucleic acids and other negatively charged molecules and for effective treatments for diseases and conditions, such as surgical adhesions.

SUMMARY OF THE INVENTION

Polymers with novel triblock structures, containing spatially separated hydrophobic and hydrophilic parts, have been developed for the effective delivery of negatively charged molecules, such as nucleic acids, to target cells.

Accordingly, in one aspect, the invention features a triblock copolymer including a hydrophilic block; a hydrophobic block; and a positively charged block capable of reversibly complexing a negatively charged molecule, e.g., a nucleic acid, wherein the hydrophobic block is disposed between the hydrophilic block and the positively charged block. Desirably, the triblock copolymer is capable of self-assembling into a supramolecular structure, such as a micelle or vesicle. In certain embodiments, the bond between the hydrophobic block and the positively charged block, e.g., a disulfide bond, vinyl ether, orthoester, acyl hydrazone, or a —N—PO$_3$— group, is labile in an endosome. The hydrophilic block may include poly(ethylene glycol), poly(ethylene oxide)-co-poly(propylene oxide) di- or multiblock copolymers, poly(ethylene oxide), poly(vinyl alcohol), polyethylene-co-vinyl alcohol), poly(N-vinyl pyrrolidone), poly(acrylic acid), poly(ethyloxazoline), poly(alkylacrylates), poly(acrylamide), poly(N-alkylacrylamides), polypeptide, polysaccharide, poly(N,N-dialkylacrylamides), hyaluronic acid, or poly(N-acryloylmorpholine). The hydrophobic block may include poly(propylene sulfide), poly(propylene glycol), esterified poly(acrylic acid), esterified poly(glutamic acid), esterified poly(aspartic acid), or a polypeptide. The positively charged block may include a polypeptide (e.g., TAT, Arg$_9$ (SEQ ID NO: 5), Lys$_9$ (SEQ ID NO: 4), or Arg-Lys copolymers), poly(ethyleneimine), or poly(amidoamine). In one embodiment, the hydrophilic block is PEG, the hydrophobic block is PPS, and the positively charged block is a polypeptide, e.g., PEG$_{45}$, PPS$_5$ or PPS$_{10}$, and TAT. The triblock copolymer may further include an internalization agent, such as transferrin, folate, a lectin, a growth factor, an RGD peptide, or a mannose-containing glycopeptide. The copolymer may further be complexed to a negatively charged molecule, e.g., a drug, a polypeptide, a synthetic or naturally occurring polymer, or a nucleic acid, such as siRNA, ODN, or a plasmid. In one embodiment, the nucleic acid is a siRNA that targets HIF-1α (e.g., GenBank Accession No. NM001530, NM 181054, or NM 017902) or PAI-1 (e.g., GenBank Accession No, X04744). In particular embodiments, the nucleic acid to be complexed with the polymer has a region of complementarity or identity to the nucleic acid sequence of a target mRNA or target gene in a cell. In further embodiments, the nucleic acid is capable of effecting a decrease in expression of protein from the target mRNA or target gene in the cell.

The invention further features a pharmaceutical composition including a triblock copolymer, as described herein, a negatively charged molecule, e.g., a nucleic acid, complexed to the triblock copolymer, and a pharmaceutically acceptable diluent.

In another aspect, the invention features a method for delivering a negatively charged molecule, e.g., a nucleic acid, to a cell including providing a triblock copolymer, as described herein, reversibly complexed to the negatively charged molecule, e.g., a nucleic acid, and contacting the cell with the triblock copolymer, wherein the triblock copolymer is internalized in the cell and delivers the negatively charged molecule to the cell. Once delivered, a nucleic acid, for example, reduces the expression of a target gene in the cell or increases the expression of a gene in the cell.

The invention also features a method for treating a disease or condition in a subject including providing a triblock copolymer, as described herein, reversibly complexed to a negatively charged molecule, e.g., a nucleic acid, and administering a therapeutically-effective amount of the triblock copolymer to the subject, wherein the triblock copolymer is internalized in a cell in the subject thereby delivering the negatively charged molecule to the cell, and treating the disease or condition in the subject. The disease or condition treated is, for example, cancer, restenosis, scar formation, or postsurgical adhesions (e.g., by delivering siRNA that targets HIF-1α or PAI-1). The negatively charged molecule, e.g., nucleic acid, may reduce or increase the expression of a protein in the cell, e.g., by decreasing expression from a target nucleic acid or by providing nucleic acid sequences capable of being expressed in the cell.

By "negatively charged molecule" is meant any molecule or ion that is capable of complexing with a positively charged polymer block. For the purposes of this specification, a negatively charged molecule does not need to possess a net negative charge, e.g., a portion of the molecule may be sufficiently negatively charged to complex, while the net charge of the molecule as a whole is neutral or positive. Exemplary negatively charged molecules include drugs, polypeptides, synthetic or other natural polymers, and nucleic acids.

By "nucleic acid" is meant any nucleobase oligomer. As is known in the art, a nucleoside is a nucleobase-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure; open linear structures are generally preferred. Within the oligonucleotide structure, the phosphate groups are commonly referred to as forming the backbone of the oligonucleotide. The normal linkage or backbone of RNA and DNA is a 3' to 5' phosphodiester linkage.

Specific examples of preferred nucleobase oligomers useful in this invention include oligonucleotides containing modified backbones or non-natural internucleoside linkages. As defined in this specification, nucleobase oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleobase oligomers.

Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity, wherein the adjacent pairs of nucleoside units are linked 3'-5' to 5'-3' or 2'-5' to 5'-2'. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other nucleobase oligomers, both the sugar and the internucleoside linkage, i.e., the backbone, are replaced with novel groups. One such nucleobase oligomer, is referred to as a Peptide Nucleic Acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Methods for making and using these nucleobase oligomers are described, for example, in "Peptide Nucleic Acids: Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In particular embodiments of the invention, the nucleobase oligomers have phosphorothioate backbones and nucleosides with heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$—, and —O—N($CH_3$)—$CH_2$—$CH_2$—. In other embodiments, the oligonucleotides have morpholino backbone structures described in U.S. Pat. No. 5,034,506.

Nucleobase oligomers may also contain one or more substituted sugar moieties. Nucleobase oligomers include one of the following at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred nucleobase oligomers include one of the following at the 2' position: $C_1$ to $C_{10}$ lower alkyl, substituted lower alkyl, alkaryl, aralkyl, O-alkaryl, or O-aralkyl, SH, $SCH_3$, OCN, Cl, Br, CN, $CF_3$, $OCF_3$, $SOCH_3$, $SO_2CH_3$, $ONO_2$, $NO_2$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of a nucleobase oligomer, or a group for improving the pharmacodynamic properties of an nucleobase oligomer, and other substituents having similar properties. Preferred modifications are 2'-O-methyl and 2'-methoxyethoxy (2'-O—$CH_2CH_2OCH_3$, also known as 2'-O-(2-methoxyethyl) or 2'-MOE). Another desirable modification is 2'-dimethylaminooxyethoxy (i.e., O($CH_2$)$_2$ON($CH_3$)$_2$), also known as 2'-DMAOE. Other modifications include, 2'-aminopropoxy (2'-$OCH_2CH_2CH_2NH_2$) and 2'-fluoro (2'-F). Similar modifications may also be made at other positions on an oligonucleotide or other nucleobase oligomer, particularly the 3' position of the sugar on the 3' terminal nucleotide or in 2'-5' linked oligonucleotides and the 5' position of 5' terminal nucleotide. Nucleobase oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleobase oligomers may also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine; 2-propyl and other alkyl derivatives of adenine and guanine; 2-thiouracil, 2-thiothymine and 2-thiocytosine; 5-halouracil and cytosine; 5-propynyl uracil and cytosine; 6-azo uracil, cytosine and thymine; 5-uracil (pseudouracil); 4-thiouracil; 8-halo, 8-amino, 8-thiol, 8-thioalkyl, 8-hydroxyl and other 8-substituted adenines and guanines; 5-halo (e.g., 5-bromo), 5-trifluoromethyl and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of an antisense oligonucleotide of the invention. These include 5-substituted pyrimidines, 6-azapyrimidines, and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are desirable base substitutions, even more particularly when combined with 2'-O-methoxyethyl or 2'-O-methyl sugar modifications. Representative United States patents that teach the preparation of certain of the above noted modified nucleobases as well as other modified nucleobases include U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692, each of which is herein incorporated by reference.

Another modification of a nucleobase oligomer of the invention involves chemically linking to the nucleobase oligomer one or more moieties or conjugates that enhance the activity, cellular distribution, or cellular uptake of the oligonucleotide. Such moieties include but are not limited to lipid moieties such as a cholesterol moiety (Letsinger et al., Proc. Natl. Acad. Sci. USA, 86:6553-6556, 1989), cholic acid (Manoharan et al., Bioorg. Med. Chem. Let, 4:1053-1060, 1994), a thioether, e.g., hexyl-S-tritylthiol (Manoharan et al., Ann. N.Y. Acad. Sci., 660:306-309, 1992; Manoharan et al., Bioorg. Med. Chem. Let., 3:2765-2770, 1993), a thiocholesterol (Oberhauser et al., Nucl. Acids Res., 20:533-538: 1992), an aliphatic chain, e.g., dodecandiol or undecyl residues (Saison-Behmoaras et al., EMBO J., 10:1111-1118, 1991; Kabanov et al., FEBS Lett., 259:327-330, 1990; Svinarchuk et al., Biochimie, 75:49-54, 1993), a phospholipid, e.g., di-hexadecyl-rac-glycerol or triethylammonium 1,2-di-O-hexadecyl-rac-glycero-3-H-phosphonate (Manoharan et al., Tetrahedron Lett., 36:3651-3654, 1995; Shea et al., Nucl. Acids Res., 18:3777-3783, 1990), a polyamine or a polyethylene glycol chain (Manoharan et al., Nucleosides & Nucleotides, 14:969-973, 1995), or adamantane acetic acid (Manoharan et al., Tetrahedron Lett., 36:3651-3654, 1995), a palmityl moiety (Mishra et al., Biochim. Biophys. Acta, 1264:229-237, 1995), or an octadecylamine or hexylamino-carbonyl-oxycholesterol moiety (Crooke et al., J. Pharmacol. Exp. Ther., 277:923-937, 1996. Representative United States patents that teach the preparation of such nucleobase oligomer conjugates include U.S. Pat. Nos. 4,587,044; 4,605,735; 4,667,025; 4,762,779; 4,789,737; 4,824,941; 4,828,979; 4,835,263; 4,876,335; 4,904,582; 4,948,882; 4,958,013; 5,082,830; 5,109,124; 5,112,963; 5,118,802; 5,138,045; 5,214,136; 5,218,105; 5,245,022; 5,254,469; 5,258,506; 5,262,536; 5,272,250; 5,292,873; 5,317,098; 5,371,241, 5,391,723; 5,414,077; 5,416,203, 5,451,463; 5,486,603; 5,510,475; 5,512,439; 5,512,667; 5,514,785; 5,525,465; 5,541,313; 5,545,730; 5,552,538; 5,565,552; 5,567,810; 5,574,142; 5,578,717; 5,578,718; 5,580,731; 5,585,481; 5,587,371; 5,591,584; 5,595,726; 5,597,696; 5,599,923; 5,599,928; 5,608,046; and 5,688,941, each of which is herein incorporated by reference.

The present invention also includes nucleobase oligomers that are chimeric compounds. "Chimeric" nucleobase oligomers are nucleobase oligomers, particularly oligonucleotides, that contain two or more chemically distinct regions, each made up of at least one monomer unit, i.e., a nucleotide in the case of an oligonucleotide. These nucleobase oligomers typically contain at least one region where the nucleobase oligomer is modified to confer, upon the nucleobase oligomer, increased resistance to nuclease degradation, increased cellular uptake, and/or increased binding affinity for the target nucleic acid. An additional region of the nucleobase oligomer may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of nucleobase oligomer inhibition of gene expression. Consequently, comparable results can often be obtained with shorter nucleobase oligomers when chimeric nucleobase oligomers are used, compared to phosphorothioate deoxyoligonucleotides hybridizing to the same target region.

Chimeric nucleobase oligomers of the invention may be formed as composite structures of two or more nucleobase oligomers as described above. Such nucleobase oligomers, when oligonucleotides, have also been referred to in the art as hybrids or gapmers. Representative United States patents that teach the preparation of such hybrid structures include U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

Locked nucleic acids (LNAs) are nucleobase oligomers that can be employed in the present invention. LNAs contain a 2'O, 4'-C methylene bridge that restrict the flexibility of the ribofuranose ring of the nucleotide analog and locks it into the rigid bicyclic N-type conformation. LNAs show improved resistance to certain exo- and endonucleases and activate RNAse H, and can be incorporated into almost any nucleobase oligomer. Moreover, LNA-containing nucleobase oligomers can be prepared using standard phosphoramidite synthesis protocols. Additional details regarding LNAs can be found in PCT publication No. WO 99/14226 and U.S. Patent Application Publication No. US 2002/0094555 A1, each of which is hereby incorporated by reference.

Arabinonucleic acids (ANAs) can also be employed in methods and reagents of the present invention. ANAs are nucleobase oligomers based on D-arabinose sugars instead of the natural D-2'-deoxyribose sugars. Underivatized ANA analogs have similar binding affinity for RNA as do phosphorothioates. When the arabinose sugar is derivatized with fluorine (2' F-ANA), an enhancement in binding affinity results, and selective hydrolysis of bound RNA occurs efficiently in the resulting ANA/RNA and F-ANA/RNA duplexes. These analogs can be made stable in cellular media by a derivatization at their termini with simple L sugars. The use of ANAs in therapy is discussed, for example, in Damha et al., Nucleosides Nucleotides & Nucleic Acids 20: 429-440, 2001.

By "reversibly complexed" is meant complexed such that the components, e.g., the positively charged block and the negatively charged molecule, disassociate under suitable conditions. Suitable conditions include under physiological conditions, such as in the cytosol or within the nucleus. The negatively charged molecule may also dissociate after the triblock copolymer has been degraded, as described herein. Under suitable conditions, at least 5, 10, 20, 30, 40, 50, 60, 70, 80, 90, or even 95% of the negatively charged molecule may dissociate from the charged block.

By "therapeutically-effective amount" is meant an amount of a triblock copolymer complexed to a negatively charged molecule sufficient to treat a disease or condition.

By "treating" is meant preventing or delaying an initial or subsequent occurrence of a disease or condition; increasing the disease-free survival time between the disappearance of a disease or condition and its reoccurrence; stabilizing or reducing an adverse symptom associated with a disease or condition; or inhibiting or stabilizing the progression of a disease or condition. This includes prophylactic treatment, in which treatment before the disease or condition is established, prevents or reduces the severity or duration of the disease or condition. In another embodiment, the length of time a patient survives after being diagnosed with a disease or condition and treated using a method of the invention is at least 20, 40, 60, 80, 100, 200, or even 500% greater than (i) the average amount of time an untreated patient survives, or (ii) the average amount of time a patient treated with another therapy survives. By "treating cancer" is meant causing a reduction in the size of a tumor, slowing or preventing an increase in the size of a tumor, increasing the disease-free survival time between the disappearance of a tumor and its reappearance, preventing an initial or subsequent occurrence of a tumor, or reducing or stabilizing an adverse symptom associated with a tumor. In one embodiment, the percent of cancerous cells surviving the treatment is at least 20, 40, 60, 80, or 100% lower than the initial number of cancerous cells, as measured using any standard assay. Preferably, the decrease in the number of cancerous cells induced by administration of a composition of the invention is at least 2, 5, 10, 20, or 50-fold greater than the decrease in the number of non-cancerous cells. In yet another embodiment, the number of cancerous cells present after administration of a composition of the invention is at least 2, 5, 10, 20, or 50-fold lower than the number of cancerous cells present after administration of a vehicle control. Preferably, the methods of the present invention result in a decrease of 20, 40, 60, 80, or 100% in the size of a tumor as determined using standard methods. Preferably, the cancer does not reappear, or reappears after at least 5, 10, 15, or 20 years. In another desirable embodiment, the length of time a patient survives after being diagnosed with cancer and treated with a composition of the invention is at least 20, 40, 60, 80, 100, 200, or even 500% greater than (i) the average amount of time an untreated patient survives or (ii) the average amount of time a patient treated with another therapy survives.

Other features and advantages will be apparent from the following description and the claims.

BRIEF DESCRIPTION OF THE DRAWINGS

FIG. 4. H-NMR in D-chloroform and gas permeation chromatography in THF were used to determine that each intermediate product in the synthetic pathway was synthesized with 100% conversion. The proton ratios and the molecular weights obtained were in agreement with expected values.

or 0% serum (D). Lipofectamine 2000 was used as a positive control. Fluorescence microscopy was used to further validate the cell internalization results with (E) showing internalization mediated by $PEG_{45}$-$PPS_5$-TAT and (F) by TAT peptide.

Figure 8:
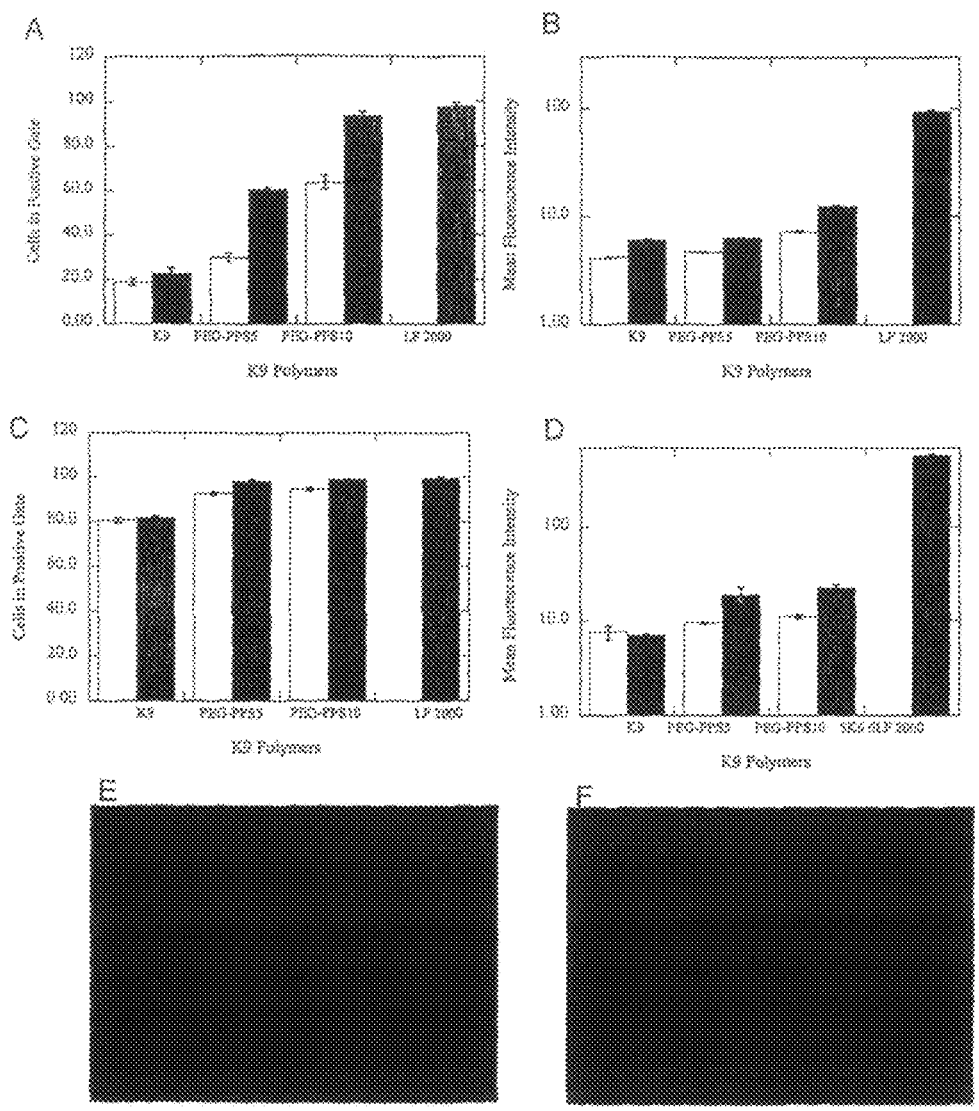

FIG. 8. Hela cell internalization of siRNA-Cy5/$PEG_{45}$-$PPS_{5,10}$-K9 polymers complexes over a 4 hour period in the presence of 10% serum (A) and 0% serum (C). The bars represent the percent of cells that have internalized the complexes when the positive gate is set so that the negative control has 5% of the cells in the gate as shown in the graphical insert. The mean fluorescence intensity is shown in for 10% serum (B) or 0% serum (D). LF2000 was used as a positive control. Fluorescence microscopy was used to validate the cell internalization results further with (E) showing internalization mediated by $PEG_{45}$-$PPS_5$-$K_9$ and (F) showing internalization mediated by $K_9$ (SEQ ID NO: 4)peptide.

Figure 9:
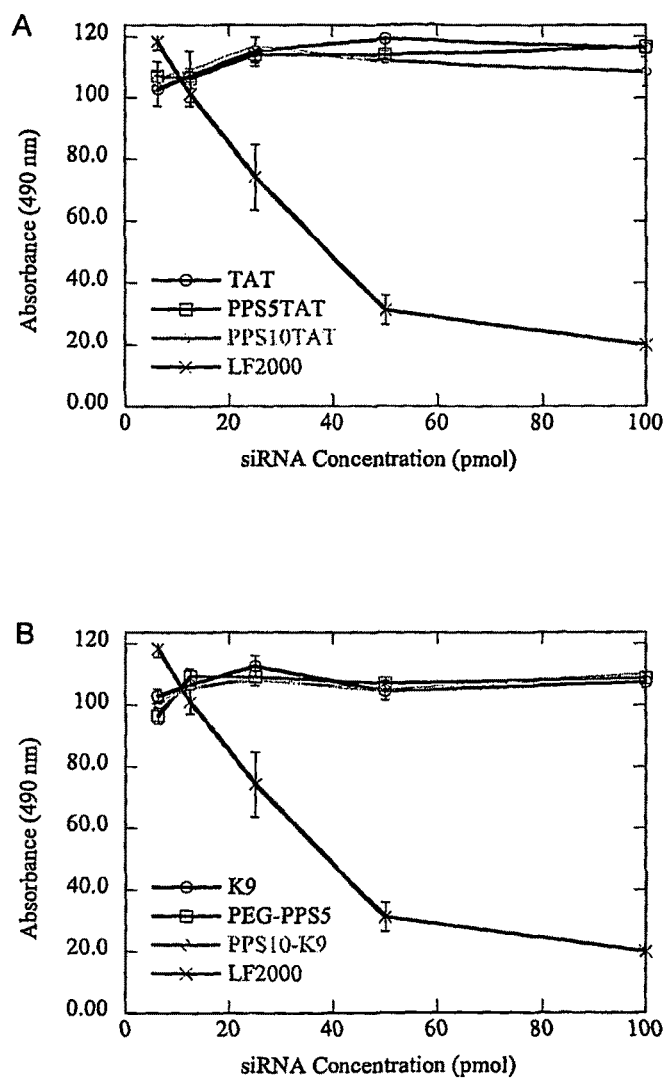

FIG. 9. To determine if the triblock copolymers were toxic the, MTT assay was used. MTT toxicity assay for (A) PEG-$PPS_{5,10}$-TAT polymers and (B) PEG-$PPS_{5,10}$-K9 polymers using LF2000 as a control are shown. Note that transfections using lipofectamine resulted in significant toxicity when more than 10 pmol of siRNA were used, while, for all the ABC triblock polymers of the invention, toxicity was minimal up to 100 pmol siRNA, the highest concentration used.

Figure 10:
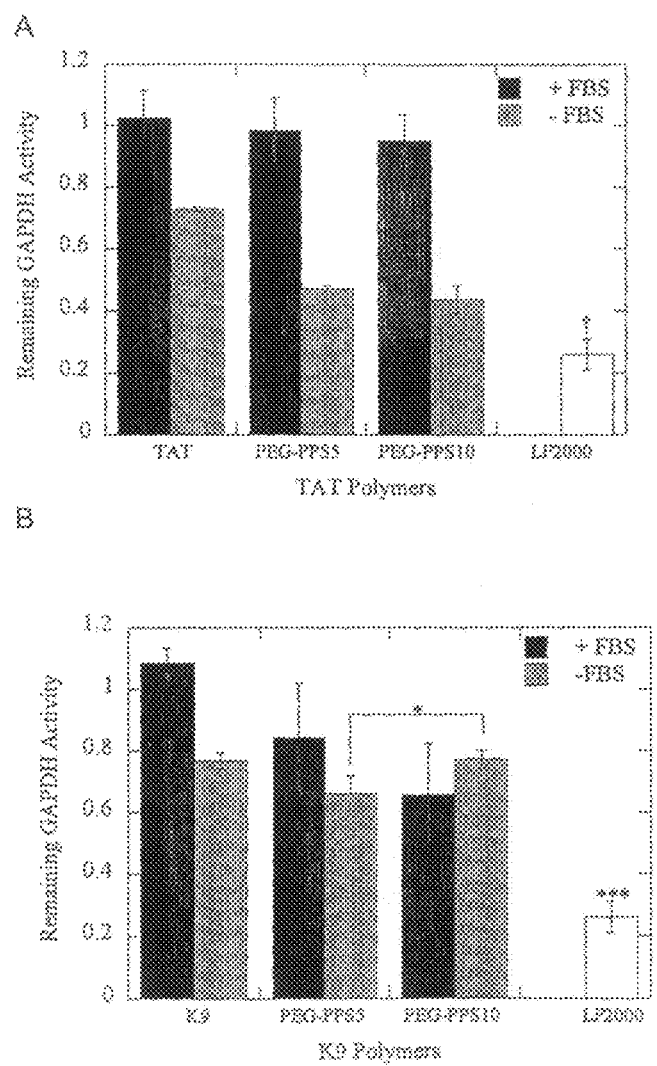

FIG. 10. siRNA GAPDH downregulation assay. Hela cells were transfected with siRNAs encoding for GAPDH enzyme using TAT based polymers (A) or K9 based polymers (B) in the presence or absence of serum. LF 2000 was used as a control. Statistical analysis was performed using multiple comparisons and the Tukey analysis. The symbols * and *** indicates statistical significance at a level of $p<0.05$ and $p<0.001$ respectively. The symbol † indicates a significance of at least $p<0.05$.

Figure 11:
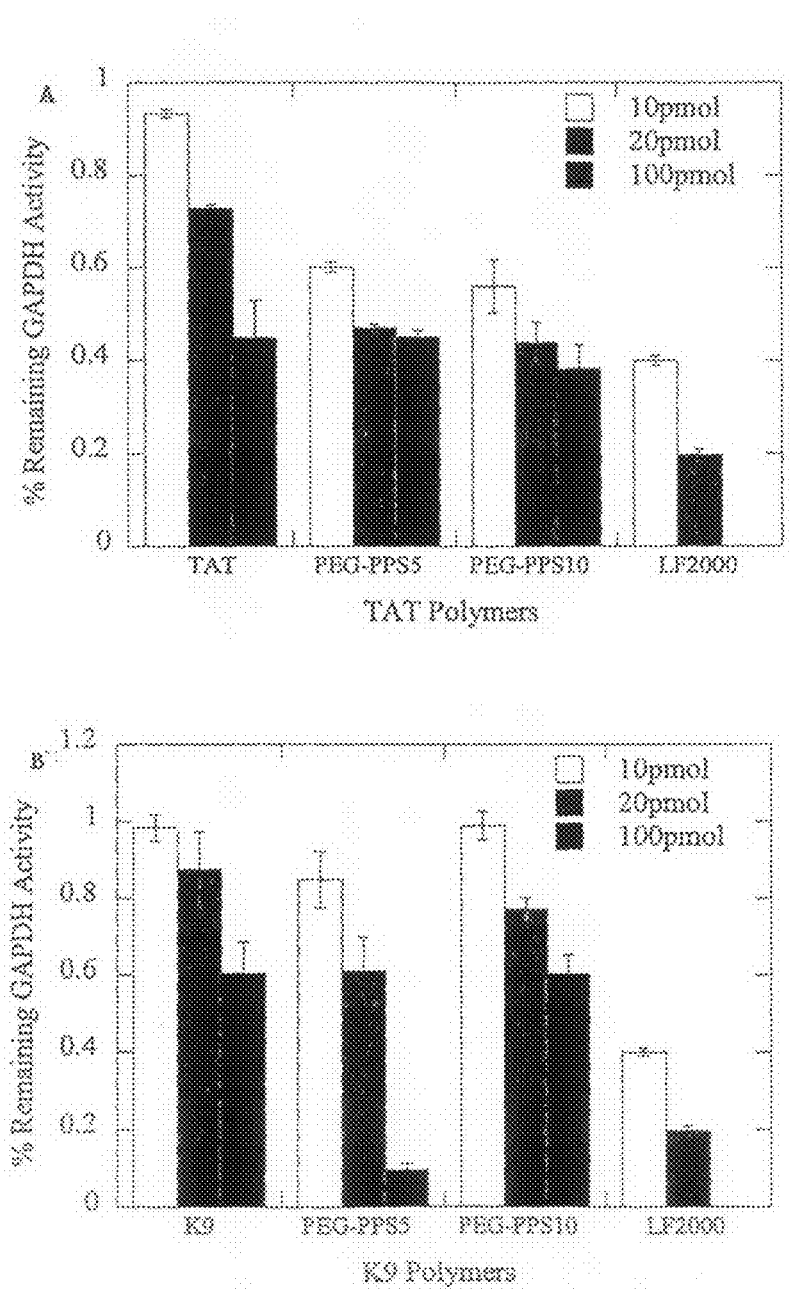

FIG. 11. siRNA GAPDH delivery at different siRNA concentrations: 10, 20, or 100 pmol. Transfections at 100 pmols with LF2000 were tried but none of the cells survived because of extreme toxicity. Transfections for PEG-PPS5, 10-TAT (A) and PEG-PPS5,10-K9 (B) show that downregulation is possible starting at the lowest concentration of complexes. At 100 pmol siRNA PEG-PPS5-K9 was able to achieve an impressive 90.5% GAPDH silencing indicating the effectiveness of this delivery strategy.

DETAILED DESCRIPTION OF THE INVENTION

The invention features triblock copolymers for the delivery of negatively charged molecules, such as nucleic acids, to cells. The copolymers may utilize biological pathways for both delivery and therapeutic action. In one embodiment, an amphiphilic triblock copolymer that self-assembles in aqueous environments into nanoscale micelles may be employed for the delivery of negatively charged molecules, such as siRNA or other nucleic acids. Moreover, a triblock copolymer of the invention can exploit changing intracellular environments for efficient delivery of the negatively charged molecule, e.g., the reductive environment of the endosome, and a biological pathway for therapeutic action, e.g., the activation of the RNAi pathway for gene silencing. The development of biologically responsive materials to induce release of a therapeutic agent within the early endosome and destabilize it holds promise for the development of delivery systems that can overcome limitations of current delivery systems.

Triblock Copolymer

In the field of drug delivery there exists an extensive interest in amphiphilic block copolymers that can self-assemble in aqueous environments into stable supramolecular structures. A variety of supramolecular structures can be generated such as micellar and vesicular assemblies both of which can be important for pharmacological applications. Extensive investigations have been conducted in poly(ethylene glycol) (PEG)-containing block copolymers such as copolymers with polypropylene glycol) [22-24] and poly (ethylethylene) [25]. Such block copolymers are generally prepared via ionic polymerization under strictly anhydrous conditions, making it difficult to obtain asymmetric block copolymers or to introduce biological molecules. Previously, we developed a novel class of amphiphilic triblock copolymers (ABA) composed of hydrophilic PEG (A) and hydrophobic PPS (B) polymer domains that may be synthesized using mild polymerization conditions that do not require extremely anhydrous conditions and that thus allow for the incorporation of relatively labile biological molecules, such as peptides and nucleic acids [26]. When these triblock copolymers contain a substantial hydrophobic portion (e.g., PPS length), e.g., about 20-45% of the length of the total of the hydrophobic and hydrophilic blocks (although in some cases smaller and larger blocks will also lead to self-assembly into micellar and other structures), they self-assemble into polymersomes of <100 nm size that have a hydrophilic PEG inner layer that may be used for the encapsulation drugs [27]. However, the formation of other supramolecular structures such as micelles is also possible by modifying the length of the hydrophobic and hydrophilic polymers. The presence of PEG in the surface of these supramolecular structures also makes the structures ideal for biological applications as their surface is protein resistant [27].

Figure 1:
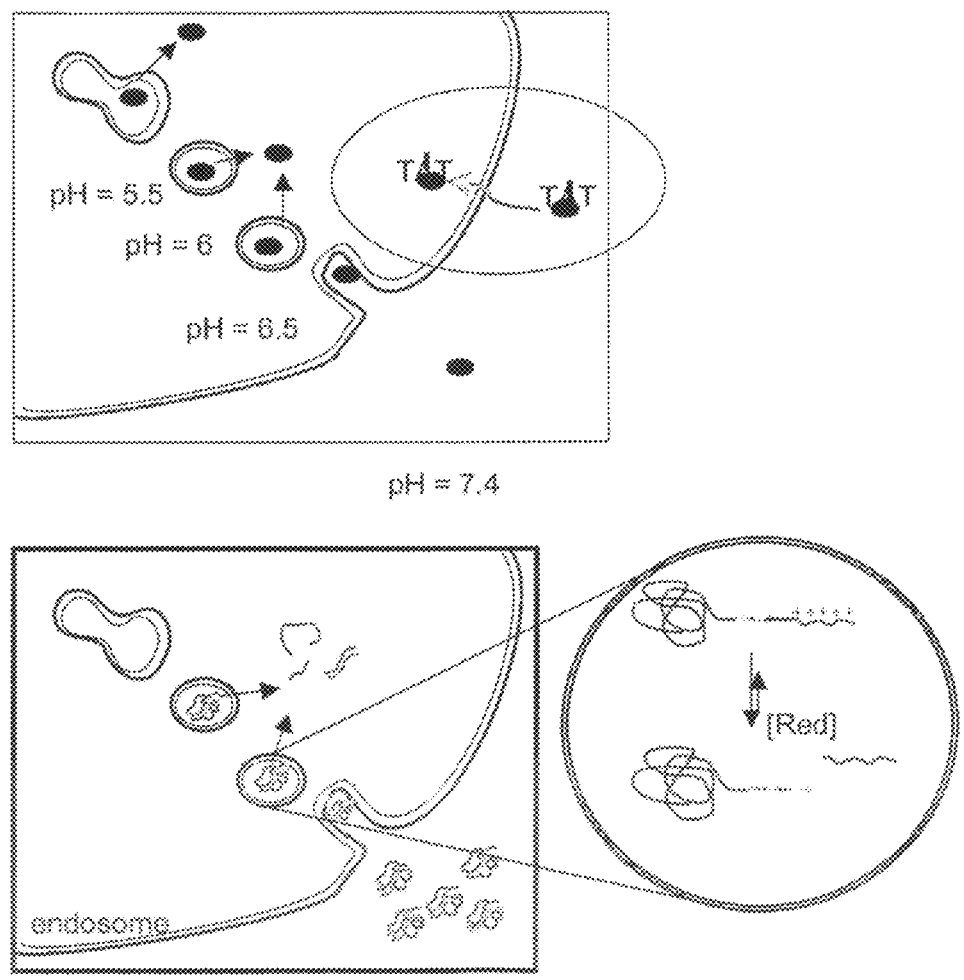
FIG. 1. Internalization and endosomal escape is a major limitation of siRNA delivery. The present invention may include two possible pathways of cellular internalization and/or endosomal escape (i) a TAT domain of HIV RKKRRQRR (residues 48-57; SEQ ID NO: 1), which have been found to enhance internalization [30,31] and (ii) a PEG-PPS polymer which may act as a surfactant and disrupt the endosomal membrane.
Figure 2:
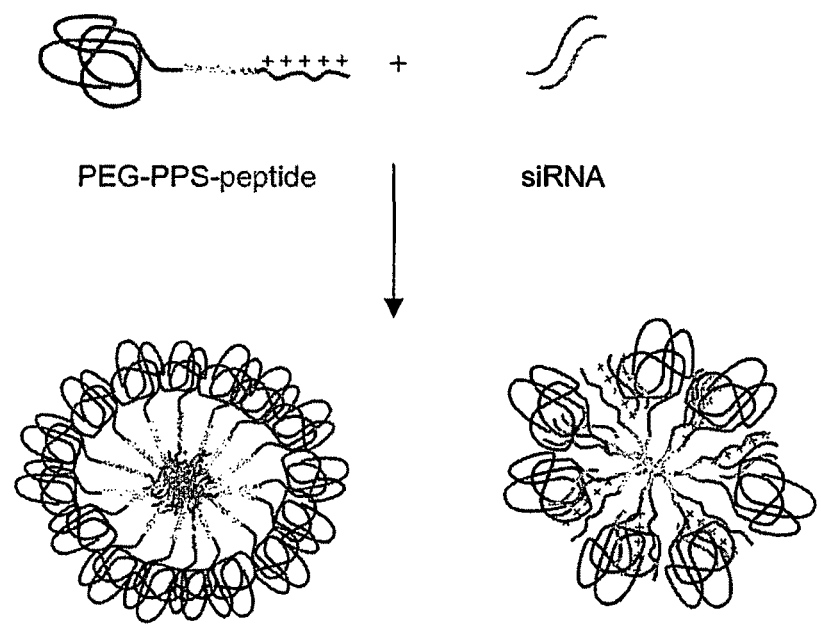
FIG. 2. One embodiment of the triblock copolymer takes advantage of the protein resistant characteristics of PEG, shielding the nucleic acid, e.g., siRNA, from enzymatic degradation. The siRNA is bound to the TAT peptide, and the complex is further stabilized by hydrophobic/hydrophilic interactions provided by PEG and PPS.

The central design underlying our approach is that a triblock copolymer (e.g., PEG-PPS-S-S-TAT) having a hydrophobic block, e.g., poly(propylene sulfide) ($PPS_x$), disposed between a hydrophilic block, e.g., poly(ethylene glycol) ($PEG_{45}$), and a positively charged block, e.g., the TAT peptide, CGGWRKKRRQRRR (SEQ ID NO: 2),can be tailored to complex negatively charged molecules, such as siRNA and other nucleic acid based drugs, via charge and hydrophilic/hydrophobic interactions (FIG. 2). Furthermore, the triblock polymer may be designed to be reductive and pH sensitive in order to take advantage of chemical differences in the cellular organelles and cellular pathways to achieve efficient delivery of siRNA or other associated payload to the cytosol (FIG. 1), or even particular organelles.

Each block of the triblock copolymer (e.g., PEG-PPSx-peptide) is important for self-assembly and biological function. The negatively charged molecule, e.g., siRNA, is bound through electrostatic interactions provided by the charged block, and the complex may be further stabilized by hydrophobic/hydrophilic interactions provided by the hydrophobic and hydrophilic blocks. The size of each block may be determined independently of the other blocks, e.g., to tailor the function of each block.

Each block may be synthesized and bound to the other blocks using methods known in the art, see for example, US 2003/0059906.

Hydrophilic Block: The hydrophilic block, e.g., PEG, may be utilized to (i) prevent non-specific negatively charged molecule/cationic polymer complex interactions with serum proteins, cells, and tissues in the body, which allows specific interactions to be designed via incorporated ligands, (ii) increase the solubility of the complexes in aqueous milieu, (iii) prevent the interaction between the negatively charged molecule/cationic polymer complexes and limit their aggregation in solution, and/or (iv) sterically protect the negatively charged molecule from enzymatic degradation. In one embodiment, the triblock copolymer employs the protein resistant characteristics of PEG, shielding the negatively charged molecule from enzymatic degradation.

Polymers or molecules that are soluble or swell in an aqueous environment will prevent protein absorption while still enhancing the solubility of the particles. For example, carbohydrate polymers such as hyaluronic acid (HA) may swell to about 1000 times their volume and are used in nature to prevent protein absorption. Other carbohydrate polymer or molecule candidates could be found from nature. Exemplary hydrophilic blocks include poly(ethylene glycol), poly(ethylene oxide)-co-poly(propylene oxide) di- or multiblock copolymers, poly(ethylene oxide), poly(vinyl alcohol), poly(ethylene-co-vinyl alcohol), poly(N-vinyl pyrrolidone), poly(acrylic acid), poly(ethyloxazoline), poly(alkylacrylates), poly(acrylamide), poly(N-alkylacrylamides), polypeptide, polysaccharide, poly(N-acryloylmorpholine), or poly(N,N-dialkylacrylamides), potentially bearing polar, ionic, or ionizable groups in the aliphatic chains Hydrophilic blocks having molecular weights between 500 and 10,000 g/mol are practical and convenient, although higher molecular weight hydrophilic blocks may be employed.

Hydrophobic block: The hydrophobic block (i) provides hydrophobic interactions that can further stabilize the self-assembled structures formed with negatively charged molecules, such as nucleic acids, and/or (ii) determines the size of the particles formed. The hydrophobic block may include any polymer or molecule that is hydrophobic in context. A preferred hydrophobic block includes PPS. Poly(propylene glycol) (PPG) is a structural homolog of PPS, with an oxygen atom instead of a sulfur atom in the backbone. Larger PPG chains may be required, relative to the useful length of PPS chains. In general, polymers that have low melting or glass transition temperatures are most desirable, in that this characteristic leads to most effective micellization.

Other polymer that are otherwise hydrophilic but are derivatized with hydrophobic functionalities on their side chains, may be used in the hydrophobic block. Examples include esterified poly(acrylic acid), esterified poly(glutamic acid) or poly(aspartic acid), and hydrophobic peptides or peptoids (e.g., N-substituted glycines). Hydrophobic blocks having molecular weights between 300 and 5000 g/mol are practical and convenient, although higher molecular weight hydrophobic blocks may also be employed.

Charged block: The charged block is employed to (i) bind nucleic acids or other negatively charged molecules via electrostatic interactions, (ii) help the self-assembled structure enter the cell, and/or (iii) have another biological function. Desirably, the charged block is sized to produce reversible binding with the negatively charged molecule, e.g., nucleic acid. Exemplary charged blocks include peptides. Peptides have been extensively utilized in the field of drug delivery and other medical applications. They have a multitude of chemical and biological functionalities that make them tremendously important in both basic science studies and clinical applications. Examples of charged peptides include the biologically active TAT peptide and oligo (lysine) (e.g., $Lys_9$; SEQ ID NO: 4) peptides. Both peptides are charged and can bind to nucleic acids and other negatively charged molecules. Additional examples of charged blocks include oligo(histidine), oligo(arginine) (e.g., $Arg_9$; SEQ ID NO: 5), and copolymers of Lys, Arg, and His. Short chain poly(ethylene imine) (PEI) may also be included in the charged block. Furthermore, poly(amidoamine) (PAMAM) dendrimers have been used to complex nucleic acids and may be included in a charged block. PAMAM has been shown to efficiently escape the endosome, allowing release of the complexed contents in the cytosol.

In certain embodiments, the charged block is sized to form a reversible complex with the negatively charged molecule, e.g., nucleic acid. For example, at least 10%, 20%, 30%, 40%, 50%, 60%, 70%, 80%, 90%, or even 95% of the molecule may dissociate from the charged block under appropriate cellular conditions, e.g., in the cytosol or within the nucleus. In addition, short charged blocks may be employed to reduce or eliminate any toxicity. Charged blocks having between 5 and 20 charges are practical and convenient, although larger blocks may also be employed. The longer the block becomes, in general the higher the corresponding cytotoxicity.

Degradation in vivo. Our triblock copolymers may be synthesized such that they respond to the changing environment of the endosome. For example, a disulfide bond may be introduced between the hydrophobic block and the charged block so that, as the environment of the endosome becomes reducing, the bond is cleaved, thereby releasing the charged domain. This release may lead to destabilization of the complex within the endosome, thus yielding more effective release of the negatively charged molecule, e.g., nucleic acid, after internalization. An $N-PO_3$ bond, which would respond to endosomal (low) pH, may also be introduced into the structure. Additional bonds, such as vinyl ether, orthoester, and acyl hydrazone, that are sensitive to intracellular degradation may also be employed.

In order to avoid irreversible accumulation in the targeted organs, the self-assembled carriers may demonstrate some form of degradation in vivo. Polysulfides are known to readily undergo oxidation to polysulfoxides and even to polysulfones, e.g., by the action of mild oxidizing agents, such as hydrogen peroxide. Under biological conditions, this oxidation can be performed extracellularly, e.g., by macrophages, or intracellularly after cellular uptake into an endosomal or lysosomal compartment. A similar kind of reaction is used for oxidizing thioether-terminated PEGs (used as emulsifiers in pulp and paper processing) in order to break wastewater foams (Wood et al., U.S. Pat. No. 4,618,400), but it has not been used in degradation in medical materials under physiological conditions.

The conversion of the polysulfides to polysulfoxides can solubilize the triblock copolymers in water, allowing elimination through excretion [32]. The conversion can trigger the instability of self-assembled aggregates, e.g. the conversion of gels to micelles or soluble polymers, the conversion of vesicles to micelles or soluble polymers, or the conversion of micelles into micelles of different size and shape or to soluble polymers. Destabilizing the aggregate can also trigger the release of the negatively charged molecule, e.g., nucleic acid. The mechanisms of clearance of soluble polymers are relatively well understood. The most important such mechanism is clearance via renal filtration, the effective molecular weight cutoff of which is approximately 30,000. Particles of size less than approximately 100 nm can be cleared from the bloodstream in the liver. Lymphatic uptake also plays an important role in clearance.

Self Assembly. Amphiphilic block copolymers have long been used as surfactants and dispersants in a wide variety of applications; the formation of organized structures in a solvent that is selective for one of the blocks is at the basis of this behavior.

Well-defined self-assembled structures, such as spherical or cylindrical micelles, lamellae, or vesicles (Booth et al., *Macromol. Chem., Rapid Commun.* 2000, 21, 501-527; Won, *Science* 1999, 283, 960-963; Discher et al., *Science* 1999, 284, 1143-1146; and Eisenberg et al., *Macromolecules* 1998, 31, 3509) have been observed in poly(oxyalkylene) block copolymers. The concentration of the polymer solution and the temperature greatly influence the kind of aggregates that can be formed: changing, e.g., from liquid spherical micellar phases to cubic phases of spherical micelles and finally to hexagonal phases of cylindrical micelles upon an increase in temperature (Mortensen, *Progr. Coll. Polym. Sci.* 1993, 93). The phase diagram and accessible structures of the amphiphilic block copolymers exhibit a dependence on the block length and number, i.e. basically, on the hydrophilic/lipophilic balance.

Block copolymers of PEG with poly(ethylethylene) have shown a propensity to form worm-like micelles at a ratio 55/45 between hydrophilic and hydrophobic repeating units (total MW=4900), and to form lamellar structures at a ratio 40:37 (total MW=3900).

In suitable conditions for the generation of micelles, the self-assembled carrier can be used for the encapsulation of hydrophobic drugs. When lamellar phases are to be formed, vesicles can be generated from the lamellar structure bending; in this way, water-dissolved drugs can be entrapped in the internal cavity of the vesicle.

This invention describes materials capable of generating a wide variety of structures; for example, a material containing long sequences of hydrophilic groups is able to form micelles, while a high hydrophobic content facilitates the formation of lamellar gels, and, under suitable conditions, vesicles.

The formation of vesicles can also be achieved by adding to water a solution or colloidal suspension of the copolymer in an organic solvent and subsequently removing the organic solvent.

Pharmaceutical Compositions. The triblock copolymers of the invention may be dispersed in a pharmaceutically acceptable diluent. In various embodiments, the pharmaceutical composition includes about 1 ng to about 20 mg of negatively charged molecule, e.g., nucleic acids, such as RNA, DNA, and plasmids. In some embodiments, the composition contains about 10 ng to about 10 mg of negatively charged molecule, about 0.1 mg to about 500 mg, about 1 mg to about 350 mg, about 25 mg to about 250 mg, or about 100 mg of negatively charged molecule. Those of skill in the art of clinical pharmacology can readily arrive at dosing amounts using routine experimentation. In addition to the negatively charged molecule, self assembled structures of the invention may include other pharmaceutically active compounds or biologically active compounds.

Suitable diluents include, but are not limited to, saline, buffered saline, dextrose, water, glycerol, ethanol, and combinations thereof. The composition can be adapted for the mode of administration and can be in the form of, for example, a pill, tablet, capsule, spray, powder, or liquid. In some embodiments, the pharmaceutical composition contains one or more pharmaceutically acceptable additives suitable for the selected route and mode of administration. These compositions may be administered by, without limitation, any parenteral route including intravenous, intra-arterial, intramuscular, subcutaneous, intradermal, intraperitoneal, intrathecal, as well as topically, orally, and by mucosal routes of delivery such as intranasal, inhalation, rectal, vaginal, buccal, and sublingual. In some embodiments, the pharmaceutical compositions of the invention are prepared for administration to vertebrate (e.g., mammalian) subjects in the form of liquids, including sterile, non-pyrogenic liquids for injection, emulsions, powders, aerosols, tablets, capsules, enteric coated tablets, or suppositories.

Methods for Internalization and Therapeutic Methods

Colloidal particles such as nanospheres, liposomes, and micelles have been studied extensively for site-specific drug delivery. Unless the reticuloendothelial system (RES) is a target, the particles must escape capture by the RES of the liver and the filtration activity of the lungs. Prolonged survival of colloidal systems in the blood has been obtained by the use of PEG-containing amphiphiles (Lasic et al., Ed. *Stealth Liposomes*; CRC Press: Boca Raton, Fla., 1995). By virtue of marked reduction of opsonization by plasma proteins, the macrophages clearance of PEG-based liposomes has been drastically reduced (Torchilin et al., *Biochim. Biophys Acta* 1994, 1195, 11-20).

A variety of internalization agents, i.e., compounds or species that enhance the internalization of the copolymers of the invention, such as antibodies, growth factors, cytokines, adhesion factors, oligonucleotide sequences, and nuclear localization sequences, has served to enhance the delivery capabilities of PEG-coated liposomes, and it has been demonstrated that the maximal activity is shown by ligands tethered to the distal end of PEG chains (Blume et al., *Biochim. Biophys. Acta* 1993, 1149, 180-184; Zalipsky et al., *Bioconjugate Chem.* 1995, 6, 705-708; Zalipsky, *J. Controlled Release* 1996, 39, 153-161; Gabizon, *Bioconjugate Chem.* 1999, 10, 289-298). This approach can be employed with the polymers of the invention. Some internalization agents can lead to very efficient cellular uptake, such as the use of growth factors, for example, fibroblast growth factor, to effect cellular uptake of DNA formulations. Other internalization agents can lead to very efficient intracellular trafficking, such as nuclear localization sequences, and these may be used in the present invention. Additional internalization agents include transferrin, folate, a lectin, a growth factor, an RGD peptide, and a mannose-containing glycopeptide.

The copolymers of the present invention are useful for any application in the controlled release, e.g., in the cytosol or nucleus, of a negatively charged molecule, e.g., nucleic acid. The advantages in using the triblock copolymers described herein are:

(i) the flexibility of the structure: with the same process and with the same family of reagents, a variety of structures can be generated;

(ii) the ease of insertion of internalization agents that enhance the selectivity of the drug delivery;

(iii) the possibility of targeted proteolytic degradation, by insertion of specific peptide sequences, or oxidative degradation, through slow oxidation or cellularly induced oxidation during cellular uptake;

(iv) the amount of PEG or other hydrophilic block that can be displayed upon the surface of a self-assembled system, in which essentially every component molecule within the system contains a grafted PEG or other opsonization-preventing hydrophilic polymer;

(v) the possibility of protecting nucleic acid and otherwise sensitive drugs within the protective environment of a self-assembled aggregate such as a micelle or vesicle, to protect the drug from degradation or clearance prior to reaching its intended target;

(vi) the possibility of triggering the release of the contents, e.g., the nucleic acid, of the self-assembled aggregate, such as a micelle or vesicle, through sensitivity of the aggregate to the environment, such as triggering a release based on the lowering of pH, increase in the extent of oxidation, and increase in the concentration of proteases during the process of intracellular trafficking from the endosome to the lysosome; and (vii) the possibility of incorporating excipients along with the nucleic acid or other negatively charged molecule to help it in reaching its final biological target, such as incorporation of agents that assist in destabilizing or permeabilizing biological membranes, such as the endosomal or lysosomal membranes, to enhance transport of the nucleic acid into the cytoplasm or ultimately into the nucleus.

In addition to nucleic acids, the polymers of the invention may be used to deliver any negatively charged molecule capable of complexing to the positively charged block. Exemplary negatively charged molecules include drugs, polypeptides, synthetic or other natural polymers, and nucleic acids. The polymers may also be employed to deliver mixtures of negatively charged molecules to a cell, e.g., two or more different nucleic acids or a nucleic acid and a drug, such as an antibiotic.

Gene-based Drugs. The triblock copolymers of the invention may be used to deliver nucleic acids for the up- or down-regulation of genes. Examples of nucleic acids include siRNA, ODN, and pDNA, including pDNA encoding therapeutic proteins.

The internalization of DNA/cationic polymer complexes can be enhanced by the covalent attachment of ligands, such as transferrin [14], folate [15], lectins [16], epidermal growth factor (EGF) [17], RGD peptides [18], and mannose-containing species such as mannose-containing glycopeptides to bind to the mannose receptor [33]. The ligand functions to direct the DNA complex to the cell surface by specifically binding to a receptor, and mediating endocytosis. Fusogenic peptides and other functional groups have been attached to enhance endosomal escape of the DNA complex [19, 20].

There exists a parallel need for delivery of other gene-based drugs, including ODN and pDNA. Here, the agent must also be delivered to the cell and its cytoplasm, and eventually to the nucleus. With ODNs, the need is even more acute, since they function by stoichiometric competition. With plasmids, the challenge is even higher, since the large size of the plasmid greatly inhibits its passage through the membranes of the cell, e.g., the plasma membrane and the endosomal membranes.

Methods for Delivering Negatively Charged Molecules. The invention provides methods for delivering a negatively charged molecule, e.g., a nucleic acid, to a cell or an animal, e.g., a mammal, or plant by contacting the cell or administering to the animal or plant a triblock copolymer complexed to the negatively charged molecule. The delivery may reduce or inhibit the expression of a target gene in a cell (e.g., a eukaryotic cell, a plant cell, an animal cell, an invertebrate cell, a vertebrate cell, such as a mammalian or human cell, or a pathogen cell). The method may be used to treat infection by a pathogen or to treat a nonpathogenic disease, e.g., cancer, postsurgical adhesions, scar formation, or restenosis after removal of arterial block (e.g., via balloon angioplasty or stenting). Typically, a nucleic acid internalized in the cell specifically reduces or inhibits the expression of a target gene, e.g., one associated with the disease (e.g., all or a region of a gene, a gene promoter, or a portion of a gene and its promoter). Exemplary pathogens include bacteria, protozoan, yeast, and fungi. In some embodiments, the nucleic acid or other molecule inhibits the expression of an endogenous gene in a vertebrate cell or a pathogen cell (e.g., a bacterial, a yeast cell, or a fungal cell), or inhibits the expression of a pathogen gene in a cell infected with the pathogen (e.g., a plant or animal cell). The nucleic acid or other molecule may also reduce or inhibit the expression of an endogenous gene, e.g., in a cancer cell or in cells that produce undesirable effects, e.g., restenosis, scar formation, and postsurgical adhesions. In some embodiments, the target gene is a gene associated with cancer, such as an oncogene, or a gene encoding a protein associated with a disease, such as a mutant protein, a dominant negative protein, or an overexpressed protein.

Alternatively, the nucleic acid or other molecule delivered may increase the expression of a gene. For example, the copolymer of the invention may be used to deliver a plasmid or other gene vector to the nucleus where one or more genes contained on the plasmid may be expressed. Such a system may be employed to enable expression of gene products that are not expressed endogenously, to increase expression of endogenous gene products, and to replace gene products that are mutated or otherwise non-functional. In some cases, local expression of these genes is mostly desired, as with, without limitation, vascular endothelial growth factor, transforming growth factor beta, platelet derived growth factor, fibroblast growth factor, insulin-like growth factor, bone morphogenetic protein, growth and differentiation factor, nerve growth factor, neurotrophin, cytokines, and transcription factors, such as hif-1alpha, runx2, and sox-9.

The nucleic acid or other molecule may reduce, inhibit, or increase expression of a target gene by at least 20, 40, 60, 80, 90, 95, or 100%. The methods of the invention may also be used to simultaneously reduce or inhibit the expression of one or more target genes while increasing the expression of one or more other target genes.

Exemplary cancers that can be treated using the methods described herein include prostate cancers, breast cancers, ovarian cancers, pancreatic cancers, gastric cancers, bladder cancers, salivary gland carcinomas, gastrointestinal cancers, lung cancers, colon cancers, melanomas, brain tumors, leukemias, lymphomas, and carcinomas. Benign tumors may also be treated using the methods of the present invention. Other cancers and cancer related genes that may be targeted are known in the art.

Exemplary endogenous proteins that may be associated with disease include ANA (anti-nuclear antibody) found in SLE (systemic lupus erythematosis), abnormal immunoglobulins including IgG and IgA, Bence Jones protein associated with various multiple myelomas, and abnormal amyloid proteins in various amyloidoses including hereditary amyloidosis and Alzheimer's disease. In Huntington's Disease, a genetic abnormality in the HD (huntingtin) gene results in an expanded tract of repeated glutamine residues. In addition to this mutant gene, HD patients have a copy of chromosome 4 which has a normal sized CAG repeat. Thus, methods of the invention can be used to silence the abnormal gene, but not the normal gene.

Exemplary diseases that may be treated with the methods include infection by pathogens, such as a virus, a bacterium, a yeast, a fungus, a protozoan, or a parasite. The nucleic acid may be delivered to the pathogen or to a cell infected with the pathogen. The pathogen may be an intracellular or extracellular pathogen. The target nucleic acid sequence is, for example, a gene of the pathogen that is necessary for replication and/or pathogenesis, or a gene encoding a cellular receptor necessary for a cell to be infected with the pathogen. Such methods may be employed prior to, concurrent with, or following the administration of the in-dwelling device to a patient to prevent infections. In-dwelling devices include, but are not limited to, surgical implants, prosthetic devices, and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, and continuous ambulatory peritoneal dialysis (CAPD) catheters.

A bacterial infection may be due to one or more of the following bacteria: *Chlamydophila pneumoniae, C. psittaci, C. abortus, Chlamydia trachomatis, Simkania negevensis, Parachlamydia acanthamoebae, Pseudomonas aeruginosa, P. alcaligenes, P. chlororaphis, P. fluorescens, P. luteola, P. mendocina, P. monteilii, P. oryzihabitans, P. pertocinogena, P. pseudalcaligenes, P. putida, P. stutzeri, Burkholderia cepacia, Aeromonas hydrophilia, Escherichia coli, Citrobacter freundii, Salmonella typhimurium, S. typhi, S. paratyphi, S. enteritidis, Shigella dysenteriae, S. flexneri, S. sonnei, Enterobacter cloacae, E. aerogenes, Klebsiella pneumoniae, K. oxytoca, Serratia marcescens, Francisella tularensis, Morganella morganii, Proteus mirabilis, Proteus vulgaris, Providencia alcalifaciens, P. rettgeri, P. stuartii, Acinetobacter calcoaceticus, A. haemolyticus, Yersinia enterocolitica, Y. pestis, Y. pseudotuberculosis, Y. intermedia, Bordetella pertussis, B. parapertussis, B. bronchiseptica, Haemophilus influenzae, H. parainfluenzae, H. haemolyticus, H. parahaemolyticus, H. ducreyi, Pasteurella multocida, P. haemolytica, Branhamella catarrhalis, Helicobacter pylori, Campylobacter fetus, C. jejuni, C. coli, Borrelia burgdorferi, V. cholerae, V. parahaemolyticus, Legionella pneumophila, Listeria monocytogenes, Neisseria gonorrhea, N. meningitidis, Kingella dentrificans, K kingae, K. oxalis, Moraxella catarrhalis, M. atlantae, M. lacunata, M. nonliquefaciens, M. osloensis, M phenylpyruvica, Gardnerella vaginalis, Bacteroides Bacteroides distasonis, Bacteroides 3452A homology group, Bacteroides vulgatus, B. ovalus, B. thetaiotaomicron, B. uniformis, B. eggerthii, B. splanchnicus, Clostridium difficile, Mycobacterium tuberculosis, M avium, M intracellulare, M leprae, C. diphtheriae, C. ulcerans, C. accolens, C. afermentans, C. amycolatum, C. argentorense, C. auris, C. bovis, C. confusum, C. coyleae, C. durum, C. falsenii, C. glucuronolyticum, C. imitans, C. jeikeium, C. kutscheri, C. kroppenstedtii, C. lipophilum, C. macginleyi, C. inatruchoti, C. mucifaciens, C. pilosum, C. propinquum, C. renale, C. riegelii, C. sanguinis, C. singulare, C. striatum, C. sundsvallense, C. thomssenii, C. urealyticum, C. xerosis , Streptococcus pneumoniae, S. agalactiae, S. pyogenes, Enterococcus avium, E. casseliflavus, E. cecorum, E. dispar, E. durans, E. faecalis, E. faecium, E. flavescens, E. gallinarum, E. hirae, E. malodoratus, E. mundtii, E. pseudoavium, E. raffinosus, E. solitarius, Staphylococcus aureus, S. epidermidis, S. saprophyticus, S. intermedius, S. hyicus, S. haemolyticus, S. hominis,* and/or *S. saccharolyticus.*

A viral infection may be due to one or more of the following viruses: Hepatitis B, Hepatitis C, picornarirus, polio, HIV, coxsacchie, herpes simplex virus Type I and 2, St. Louis encephalitis, Epstein-Barr, myxoviruses, JC, coxsakieviruses B, togaviruses, measles, paramyxoviruses, echoviruses, bunyaviruses, cytomegaloviruses, varicella-zoster, mumps, equine encephalitis, lymphocytic choriomeningitis, rhabodoviruses including rabies, simian virus 40, human polyoma virus, parvoviruses, papilloma viruses, primate adenoviruses, coronaviruses, retroviruses, Dengue, yellow fever, Japanese encephalitis virus, BK, Retrovirus, Herpesvirus, Hepadenovirus, Poxvirus, Parvovirus, Papillornavirus, and Papovavirus. The target viral nucleic acid sequence is, for example, necessary for replication and/or pathogenesis of the virus in an infected cell. Such viral target genes are necessary for the propagation of the virus and include, e.g., the HIV gag, env, and pol genes, the HPV6 LI and E2 genes, the HPV II LI and E2 genes, the HPV 16 E6 and E7 genes, the BPV 18 E6 and E7 genes, the HBV surface antigens, the HBV core antigen, HBV reverse transcriptase, the HSV gD gene, the HSVvp 16 gene, the HSV gC, gH, gL and gB genes, the HSV ICPO, ICP4 and ICP6 genes, Varicella zoster gB, gC and gH genes, and the BCR-abl chromosomal sequences, and non-coding viral polynucleotide sequences which provide regulatory functions necessary for transfer of the infection from cell to cell, e.g., the HIV LTR, and other viral promoter sequences, such as HSV vp 16 promoter, HSV-ICPO promoter, HSV-ICP4, ICP6 and gD promoters, the HBV surface antigen promoter, the HBV pre-genomic promoter, among others.

The copolymers of the invention can be used to treat subjects already infected with a virus, such as HIV, in order to shut down or inhibit a viral gene function essential to virus replication and/or pathogenesis, such as HIV gag. Alternatively, this method can be employed to inhibit the functions of viruses, which exist in mammals as latent viruses, e.g., Varicella zoster virus, the causative agent of shingles. Similarly, diseases such as atherosclerosis, ulcers, chronic fatigue syndrome, and autoimmune disorders, recurrences of HSV-I and HSV-2, HPV persistent infection, e.g., genital warts, and chronic BBV infection among others, which have been shown to be caused, at least in part, by viruses, bacteria, or another pathogen, can be treated according to this method by targeting certain viral polynucleotide sequences essential to viral replication and/or pathogenesis in the mammalian subject.

Preferably, the nucleic acid or other molecule is administered in an amount sufficient to treat the disease or condition, e.g., to prevent, stabilize, or inhibit the growth of the pathogen or to kill the pathogen or to increase or decrease the expression of an endogenous gene whose under- or overexpression results in a disease.

EXAMPLES

Polymer Synthesis

PEG-allyl Synthesis: PEG45 monomethyl ether (PEG45) was modified with allyl bromide as previously described with modifications [26]. In short, PEG45 (20 g, 10 mmol) was dissolved in tetrahydrofuran (THF, 300 mL) under inert atmosphere and heated to reflux for 3 to 4 hours in a Soxhlet apparatus filled with molecular sieves. The solution was allowed to cool to the touch, and 2.5 equivalents (0.6 g, 25 mmol) were added. The solution was stirred and allowed to react for 15 min before 1.4 mL (3.46 g, 40 mmol) of allyl bromide was added to the solution under stirring and allowed to react for 24 hours. The reaction mixture was passed through a filter cake to remove the NaBr salt formed during the reaction. The solution was then evaporated and precipitated two times in diethyl ether. A white solid polymer was obtained (16.68 g, 83.4% yield, conversion 100%). H NMR (CDCl3): δ 3.56-3.7 (broad, PEG polymer protons), 3.41 (S, 3H, —OCH3), 4.01-4.04 (dd, 2H, —H2OCH2CH=CH2), 5.15-5.30 (m, 2H, —CH2OCH2CH=CH2), 5.85-5.98 (m, 1H, —CH2OCH2CH=CH2).

PEG-thioacetate synthesis: PEG-allyl ether was modified with thioacetic acid to form PEG-thioacetate as previously described with modifications [26]. PEG-allyl ether (8 g, 4 mmol) was introduced to a Schlenck tube in toluene (64 mL). The toluene was degassed with sonication for 20 minutes and bubbling with argon gas for 30 min. The PEG/toluene solution was further degassed with pump evacuation and filling the Schlenck tube with argon. This procedure was repeated 3 times. The reaction mixture was then warmed to 60° C., and the first of five AIBN aliquots was added (1.3 g×5, 0.8 mmol×5) followed by the first of five thioacetic acid aliquots (0.456 mL'5, 6.4 mmol×5). The five aliquots were added over an 8 to 10 hour period. The reaction was allowed to continue for 18 hours at 60° C. and an additional 24 hours at room temp. The reaction mixture was mixed with activated DOWEX 1/8-100 (Cl) resin and incubated for 1 hour. After filtration, the solution was solvent evaporated and then precipitated three times with diethyl ether. Dichloromethane ($CH_2Cl_2$) was used to re-dissolve the precipitate. A slightly pale yellow solid was obtained (5.26 g, 65.7% yield, conversion 90%). H NMR (CDCl3): δ 1.81-1.90 (q, 2H, —OCH2CH2CH2S—), 2.35 (s, 3H, —SCOCH3), 2.92-2.97 (t, 2H, —OCH2CH2CH2S—), 3.39-3.89 (broad, PEG chain protons), 3.41 (s, 3H, —OCH3).

Figure 3:
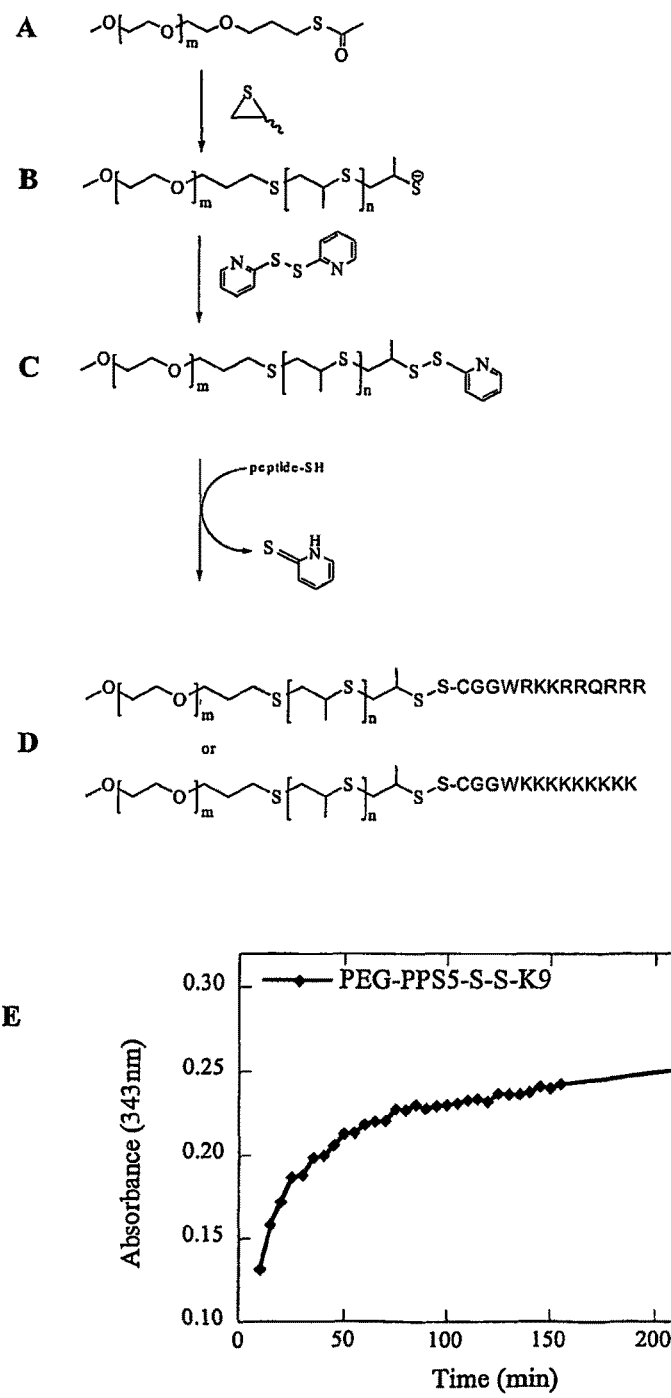
FIG. 3. Synthetic scheme of poly(ethylene glycol)-poly (propylene sulfide)-peptide(PEG-PPS -peptide). PEG-thioacetate (A) is activated by sodium methoxilate to form a sulfide that can drive the anionic polymerization of propylene sulfide to form B. 2,2'-Dipyridyl disulfide was used as the end capping agent to generate the AB diblock copolymer with the mixed pyridyldisulfide (C). The peptides TAT (CG GWRKKRRQRRR; SEQ ID NO: 2) and K9 (CGGWKK-KKKKKKK; SEQ ID NO: 3) reacted with C via a disulfide exchange reaction to generate the ABC triblock copolymers shown (D). The formation of the triblock copolymer was monitored by recording the absorbance at 342 nm, which corresponded to the release of pyridine thione (E).

PEG-PPS diblock polymer synthesis: The polymer $PEG_{45}$-$PPS_x$-pyridyldithio was synthesized using anionic polymerization of propylene sulfide (PS) with 2,2-dipyridine dithione as the end-capping agent to form PEG-PPS-pyridyl-dithio (FIG. 3). PEG-thioacetic acid (1 g, 0.5 mmol) was dissolved in dry THF (23 mL). Sodium methoxylate (NaMeOH, 1.1 mL, 0.55 mmol) was added to the solution and allowed to react for 30 minutes. PS (0.394 mL, 5 mmol or 0.196 mL, 2.5 mmol) was added via syringe and allowed to react for 1.5 hours. Dipyridine dithione (0.44 mg, 2 mmol) was dissolved in THF and added to the reaction mixture via syringe. The progress of the reaction can be easily followed by the appearance of an intense yellow color. After filtration and solvent evaporation the product was precipitated in diethyl ether. A pale yellow solid was obtained (336.2 mg, 33.6% yield, n=5.056 and 284 mg, 28.41% yield, n=9.648). H NMR (CDCl3): δ 1.35-1.45 (d, CH3 in PPS chain), 1.81-1.90 (broad q, 2H —OCH2CH2CH2S), 3.6-3.7 (broad PEG chain protons), 7.8-7.83 (m, 1H pyridine group). The degree of polymerization of the PPS block was determined by taking the ratio of PEG protons to PPS protons, resulting in polymers with n=5.056 and n=10.708. The Polydispersity index (PDI) of the polymers was determined by GPC with PDI=1.147 and PDI=1.259 for n=5.056 and n=10.708 respectively.

PEG-PPS-peptide triblock polymer synthesis: The peptides Ac-CGGWRKKRRQRRR-NH2 (TAT; SEQ ID NO: 2) and Ac-CGGWKKKKKKKKK-NH2 (K9; SEQ ID NO: 3) were bound to the $PEG_{45}$-PPS-pyridyldithio polymers using a disulfide exchange reaction between the disulfide end capping PEG-PPS and the cysteine group of the peptide. The course of the reaction was monitored following the release of 2-pyridinethione at 342 nm (see E in FIG. 3). Upon dilution in $D_2O$ at 12 mg/mL, the solution turned cloudy indicating the formation of aggregates. Furthermore, upon dilution in $CDCl_3$ at 12 mg/mL, the solution again turned cloudy with a green color indicating the formation of aggregates and the strong amphiphilic nature of the molecule. H NMR in water: δ 1.35-1.45 (d broad, $CH_3$ in PPS chain), 1.81-1.90 (broad peak no q visible and signal integration reduced, 2H —$OCH_2CH_2CH_2S$), 3.6-3.7 (broad PEG chain protons unchanged). Protons from the peptide were not observed. H NMR in $CDCl_3$: δ 1.35-1.45 (broad no d visible, $CH_3$ in PPS chain), 1,81-1.90 (q, 2H —$OCH_2CH_2CH_2S$), 3.6-3.7 (broad PEG chain protons), 7.08-7.13 and 7.2-7.24 (t, tryptophan amino acid residue) and 7.5-7.54 and 7.6-7.64 (d, tryptophan amino acid residue).

Summary of Polymer Synthesis and Characterization

The ABC triblock copolymer PEG-PPS-peptide was synthesized using the anionic polymerization of propylene sulfide to an activated PEG-thiol under an inert atmosphere (FIG. 3). The addition of the peptide was done using a disulfide exchange reaction in aqueous atmosphere. The reaction was monitored using the release of 2-pyridine dithione at 342 nm, resulting in the reaction reaching a plateau after two hours (see E in FIG. 3). After each step, the synthesis was characterized with H-NMR to confirm that the correct product was achieved and that there were no remaining impurities. At the concentrations required for H-NMR analysis, however, the triblock polymer formed aggregates, likely micelles, in both an aqueous environment ($D_2O$) or in D-Chloroform, because of its strong amphiphilic nature. H-NMR of the triblock contained wide signals that were difficult to integrate and measure and resulted in lower integration numbers than were expected if no aggregates were formed. Synthesis was also confirmed by gel permeation chromatography. FIG. 4 shows H-NMR in D-chloroform and gas permeation chromatography in THF used to determine that each intermediate product in the synthetic pathway was synthesized with 100% conversion. The proton ratios and the molecular weights obtained were in agreement with expected values.

Figure 6:
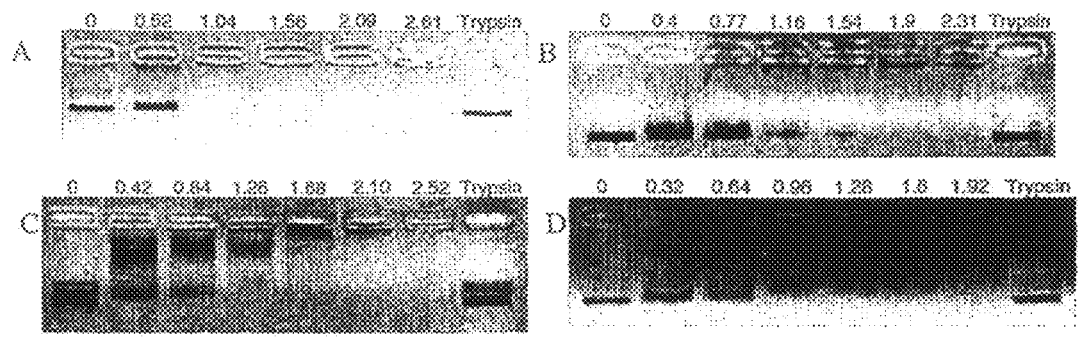
FIG. 6. The ability of $PEG_{45}$-$PPS_5$-TAT and $PEG_{45}$-$PPS_5$-$K_9$ to self assemble with plasmid DNA was assessed via gel electrophoresis. To a DNA solution in TBS (20 µg/mL) small fractions of the condensing polymer were added. After each addition a fraction was removed to run in a gel to assess the extent of complexation. (A) TAT peptide (B) $K_9$ peptide (SEQ ID NO: 4) (C) $PEG_{45}$-$PPS_5$-TAT triblock polymer (D) $PEG_{45}$-$PPS_5$-$K_9$ triblock polymer. The gels show that the triblockcopolymers are able to self assemble with DNA to form particles that do not migrate in an agarose gel. To prove further that the triblock polymers formed condensed structures with siRNA a fluorescence reduction assay was employed. The relative fluorescence intensity of siRNA-EtBr was measured with increasing amounts of $PEG_{45}$-$PPS_{5,10}$-TAT (E) or $PEG_{45}$-$PPS_{5,10}$-K9 (F) being added. The fluorescence intensity decreased as more polymer was added until a plateau was reached indicating that particles had formed. The dotted line indicates the charge ratio at which complex migration in agarose gel electrophoresis was stopped.
Figure 6:
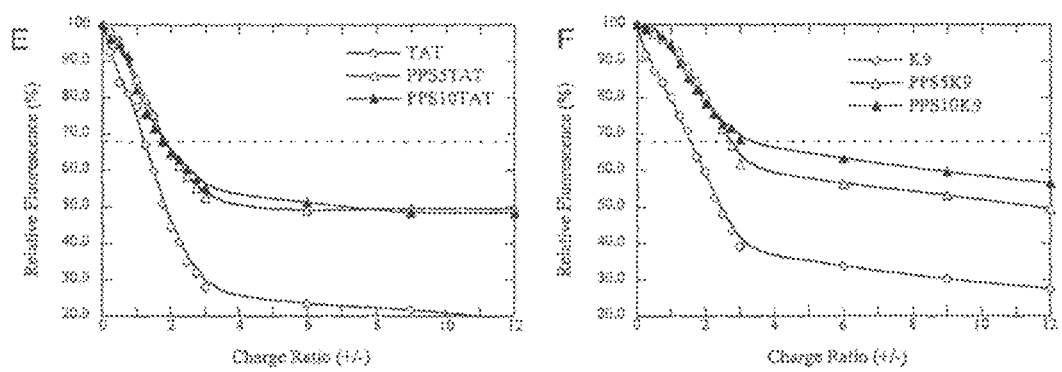

Fluorescence reduction assay: The ability of PEG-PPS-peptide to form complexes with siRNA was tested using a gel electrophoresis and ethidium bromide (EtBr) fluorescence reduction assay (FIG. 6). siRNA (150 pmol, 100 µL) was mixed with EtBr and the resulting fluorescence emission was measured using a fluorescence microplate reader (Tecan, Germany). The reduction of fluorescence emission was measured as triblock copolymer was added to generate the indicated charge ratio. All polymers were able to exclude EtBr from the siRNA as more polymer was added (higher charge ratios), indicating that condensed particles are forming. Both peptides TAT and K9 when used alone resulted in the most condensed particles reaching up to an 80% decrease in fluorescence intensity. Triblock copolymers based on TAT (FIG. 6E), showed little difference in their ability to form condensed particles with siRNA with the maximum fluorescence decrease being reached at a charge ratio of 3 with 50% decrease. Triblock copolymers based on K9 (FIG. 6F), on the other hand, showed more of an effect of PPS length with PPS5 resulting in more condensed structures than PPS 10. The maximum fluorescence decrease was also 50%.

Size and Zeta Potential characterization: The ability of PEG-PPS-peptide alone or in solution with siRNA to form nano-sized aggregates was studied using dynamic light scattering (DLS) in a nano-zetasizer (Malvern, UK). Size measurements of triblock polymers alone were measured dissolving the individual polymers in Tris Buffer Saline (TBS) at a 10 mg/mL and using the standard settings in the instrument. For PEG-PPS-peptide/siRNA size measurements complexes were formed adding the triblock polymer solution (150 µL) to a siRNA solution (150 pmol, in 150 µL TBS) at different charge ratios. 100 µL of the solution was used to measure size and the other was dissolved in MiliQ water to 1000 µL and used to measure zeta potential of the complexes.

In the absence of siRNA, the triblock polymers PEG-PPS5-TAT, PEG-PPS10-TAT, PEG-PPS5-K9, PEG- PPS10K9 formed aggregates in solution at a concentration of 10 mg/mL, with sizes of 11.3±0.4, 16.0±0.25, 13.1±0.08 and 16.0 ±0.57 nm respectively. There was a statistical significance between the size of PEG-PPS5-peptide and PEG-PPS10-peptide aggregates for both TAT and K9 with p<0.001, indicating that the size of the PPS unit affects the overall size of the particles formed. Furthermore, for triblock with PPS degree of polymerization of 5 (n=5), there was a statistical difference of the size of aggregates formed between TAT and K9 p<0.01, indicating that the character of the peptide also affects the size of the resulting aggregates.

Figure 5:
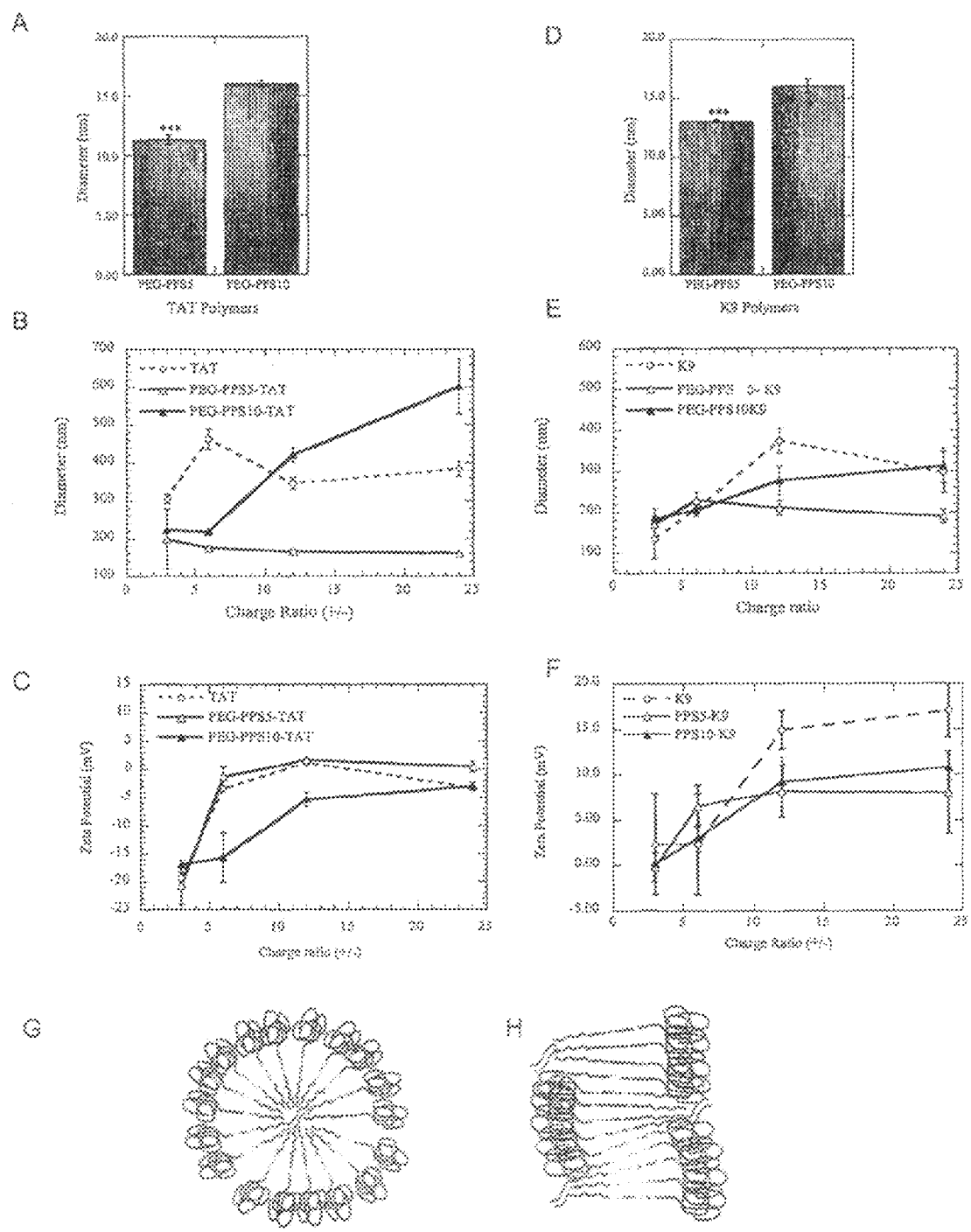
FIG. 5. Upon dissolving the triblock copolymers in water (10 mg/mL) the polymers aggregated into particles. The mean diameter of $PEG-PPS_{5,10}$-TAT (A) and $PEG-PPS_{5,10}$-K9 (D) are shown. The polymers were mixed with siRNA at concentrations below their critical micelle concentration, and the resulting aggregates were analyzed for size (B, E) and zeta potential (C, F) as a function of charge ratio. G and H illustrate how triblock polymers with different PPS domain sizes may aggregate differently.

Size and surface charge of the aggregates formed between siRNA and PEG-PPS5-TAT, PEG-PPS 10-TAT, PEG-PPS5-K9, PEG-PPS10K9 and TAT and K9 were measured using DLS and zeta potential (FIG. 5). Complex size was found to be dependent on the amount of polymer used (charge ratio) and the length of the hydrophobic block (PPS). For both of the peptides tested and for triblock polymers with a small PPS block (PPS5), the size of the particles formed decreased as the amount of polymer increased with sizes ranging from 199.0±79.3 to 160.2±1.45 nm for PEG-PPS5-TAT (FIG. 5B, open triangles) and 170.5±38.2 to 188.8±16.5 nm for PEG-PPS5-K9 (FIG. 5E, open triangles). However, for the triblock polymers were the PPS unit was longer (PPS10) the trend was reversed, increasing the polymer content increased the size of the particles with particle size ranging from 222.2±0.75 to 601.2±72.83 nm and 312.3±42.73 nm for PEG-PPS10-TAT (FIG. 5B, closed triangles) and PEG-PPS10-K9 (FIG. 5E, closed triangles) respectively. Zeta potential for particles formed with TAT polymers increased from negative ~−20 mV to ~0 mV and for K9 polymers started out at ~0 mV and increased up to ~+10 mV.

Figure 7:
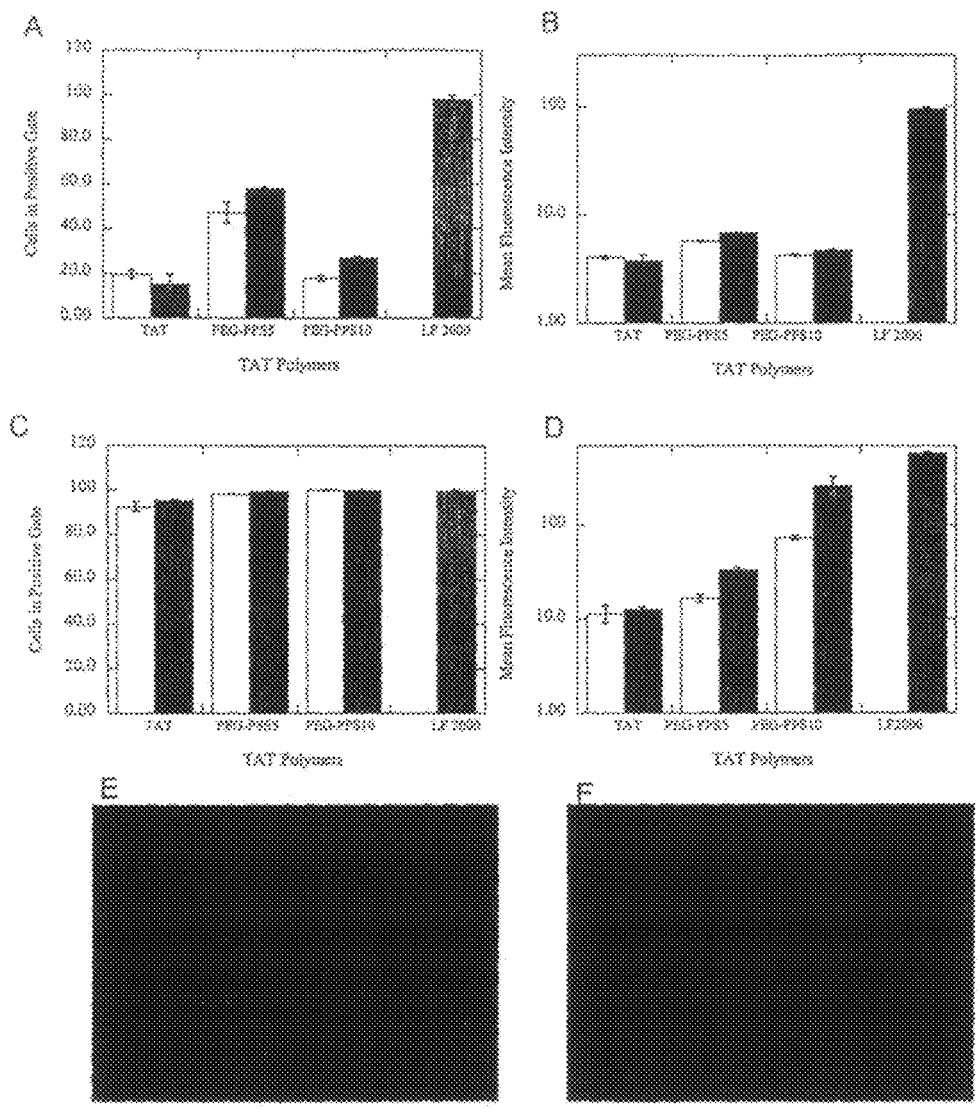
FIG. 7. FACS analysis of Hela cell internalization of siRNA-Cy5/$PEG_{45}$-$PPS_{5,10}$-TAT polymers complexes over a 4 hour period in the presence of 10% serum (A) and 0% serum (C). The bars represent the percent of cells that have internalized the complexes when the positive gate is set so that the negative control has 5% of the cells in the gate. The mean fluorescence intensity is shown in for 10% serum (B)

PEG-PPS-peptide/siRNA Internalization Studies: Cell internalization studies were assessed via fluorescence microscopy (Zeiss, Feldbach, Switzerland) and fluorescence activated cell sorting (FACS). Hela cells (40,000 cells/well, 24-well plate) were seeded the day before adding complexes with siRNA labeled with Cy3 (microscopy) or Cy5 (FACS). On the day of transfection, siRNA/polymer complexes (25 pmol siRNA) were formed at a charge ratio of 6 for the microscopy studies and 3 or 6 for the FACS studies and added to the cells and incubated with the cells for either 24 for the microscopy experiments or 4 hours for FACS experiments. After the incubation the cells were washed three times with PBS and either visualized using a fluorescence microscope or trypsinized, centrifuged, and resuspended in 1% FBS in PBS. The cells were not fixed. Untreated cells were used to determine the native background of the cells and to adjust the gates. The live cell gate was adjusted so that 10,000 events were read. The positive cell gate was defined as having less than 0.5% positive cells for untreated cells (a 95% confidence interval). To compare internalization using FACS data the mean fluorescent intensity of each cell population was normalized to the background fluorescent of untreated cells (FIGS. 7 and 8). FACS data were analyzed by determining the number of cells in the positive gate and the total mean fluorescence intensity of the cell population. Cellular internalization of PEG-PPS-peptide complexes was affected by serum, with internalization in the presence of serum giving up to a 60% or 93% cells taking up complexes for PEG-PPS5-TAT (+/−6) and PEG-PPS10-K9 (+/−6) respectively (FIGS. 7A and 8A). In contrast, in the absence of serum all complexes were internalized by >90% of the cells. Interestingly, the K9 family of polymers was less affected by serum than the TAT family of polymers. In serum containing conditions, the amount of internalization for all triblock polymers was affected by the charge ratio with higher charge ratios (+/−6) resulting in more cells internalized than low charge rations (+/−3).

The mean fluorescence intensity (MFI) of the cells was affected by the presence of serum, length of the PPS, and charge ratio of the complexes. In general, longer PPS domains and higher charge ratio achieved more particle internalization (higher MFI) than short PPS domains or lower charge ratio. Interestingly, MFI was also affected by the type of peptide used with the TAT peptide being more affected by serum than the K9 peptide. In the presence of serum, the maximum MFI observed was of 12.4±0.08 for PEG-PPS10-K9 compared to 94.9±2.2 for LF2000. In the absence of serum, the internalization by the PEG-PPS-K9 polymers only increased moderately with the maximum MFI being 22.4±1.6 for PEG-PPS 10-K9 compared to 580±14.53 for LF2000 (FIG. 8B). For PEG-PPS-TAT polymers the increase of complex internalization in the absence of serum was more considerable with the maximum MFI being 263.3±68.8 compared to 580±14.53 for LF2000 (FIG. 7B).

Toxicity of PEG-PPS-peptide/siRNA complexes: The toxicity of the triblock polymer/siRNA complexes was assessed using the MTT assay (Promega Corp, Madison, Wis.). Hela cells (7,000 cells/well) were plated on a 96 well plate the day before they were exposed to the triblock copolymers/siRNA complexes. To determine the effect of complex concentration on toxicity, different siRNA concentrations were delivered with complexes at a charge ratio of 6. Complexes were incubated with the cells for 24 hours then removed, and new media added. The MTT solution (20 µL) was added to each well and incubated for 2 hours. Absorbance readings were measured at 490 nm. Untreated cells were used as the 100% cell proliferation control, and LF2000 was used as a comparative control using a 20 pmol siRNA/µL LF2000. None of the concentrations used for the different triblock copolymer/siRNA transfections resulted in a reduction of cell proliferation indicating that no toxicity occurred as a result of the complexes (FIG. 9). In contrast LF2000/siRNA complexes resulted in significant toxicity at concentrations of more than 10 pmol/well.

GAPDH Gene Downregulation: The efficacy of the delivery strategy was studied using a GAPDH enzyme activity assay (Ambion). Hela cells (7,000 cells/well) were plated in 96-well plates the day before transfection and transfected with 10 pmol siRNA at a charge ratio of 6. The transfections occurred both in the presence and absence of FBS (0% or 10%) and in the presence and absence of chloroquine (Sigma, 100 µM). Before transfection, the cell medium was replaced with transfection medium. For complexation, siRNA (30 pmol, 60 µL OptimMem) was mixed with the triblock or unmodified peptide polymer (60 µL, TBS) and mixed by vortexing for 10 seconds. The mixture was allowed to form undisturbed for 10 min. The extent of gene down-regulation was assessed 48-hours post transfection. LF2000 complexes were formed using a 1 µL of LF2000 to 20 pmol of siRNA. To determine if the transfection procedure affected GAPDH expression, a non-targeting sequence of siRNA was used (siNEG). GAPDH activity was only significantly reduced when LF2000 was used as the delivery vector for siNEG. The remaining GAPDH activity was measured as described by the manufacturer using kinetic fluorescence increase method over five minutes and was calculated according to the following equation % remaining expression=$\Delta_{fluorescence,\ GAPDH}/\Delta_{fluorescence,\ siNEG}$ where $\Delta_{fluorescence}$=Fluorescence$_{1\ min}$−Fluorescence$_{5\ min}$ for either transfected (GAPDH), mock transfected (siNEG), or untransfected cells. Untransfected cells are cells that are exposed to serum or non-serum media for the 4 hours of transfection and then replaced with cMEM. For LF2000, the control is a mock transfection using siNEG to determine the level of down-regulation that occurs because of the transfection procedure.

The ability of PEG-PPS-peptide/siRNA complexes to mediate gene down-regulation of GADPH enzyme in vitro in the presence and absence of serum was investigated at 20 pmol/well siRNA (FIG. 10). In the presence of serum, no significant amount of down-regulation was observed. In the absence of serum, however, significant downregulation was observed for all triblock polymers with PEG-PPS5-TAT and PEG-PPS10-TAT achieving a 53±0.009 and 56.2±0.05 GAPDH gene down-regulation respectively. PEG-PPS5-TAT and PEG-PPS 10-TAT were statistically more able to mediate gene down-regulation than the TAT peptide alone. Interestingly, the K9 polymers in general were not as able to mediate gene down-regulation as the TAT polymers achieving at most a 34%±0.06 GAPDH gene down-regulation down-regulation for PEG-PPS5-K9. PEG-PPS5-K9 was statistically more able to mediate gene down-regulation than K9 and PEG-PPS 10-K9.

To determine the effect of siRNA complex concentration on transfection efficiency, transfections were performed using 10, 20, or 100 pmol of siRNA at a charge ratio of 6 and in the absence of serum (FIG. 11). An increase in complex concentration from 10 to 20 pmol statistically significantly affected GAPDH down-regulation of all complexes tested including LF2000. However, an increase from 20 to 100 pmol only resulted in an enhanced GAPDH down-regulation for the K9 family of polymers and not for the TAT family of polymers indicating a different mechanism of action. Down-regulation using PEG-PPS$_5$-K9 at 100 pmols resulted in a down-regulation level of 90.5% without toxicity as assessed by the MTT assay (see above). In contrast, transfection with LF2000 at 20 pmol resulted in down-regulation at a level of 80% with significant toxicity. For LF2000 transfections at 100 pmols resulted in complete cell death.

Incorporation of Internalization Agents: Internalization agents can be introduced to the triblock copolymer by using a bifunctional hydrophobic block, e.g., PEG, rather than a monofunctional one to start the reaction. The bifunctional PEG, NHS-PEG-Melamide, is used. RGD, folate, or another internalization agent is bound to the bifunctional PEG via carboxylic acid/amine chemistry (NHS end). The melamine may then be modified with a bifunctional thiol group which contains free thiols at either end so that the molecule RGD-PEG-SH is generated. The normal PPS-TAT synthesis can then be performed.

REFERENCES

1. McCaffrey, A. P., et al., *RNA interference in adult mice*. Nature, 2002. 418(6893): p. 38-9.
2. Hill-West, J. L., et al., *Prevention of postoperative adhesions in the rat by in situ photopolymerization of bioresorbable hydrogel barriers*. Obstet Gynecol, 1994. 83(1): p. 59-64.
3. Elbert, D. L. and J. A. Hubbell, *Reduction of fibrous adhesion formation by a copolymer possessing an affinity for anionic surfaces*. J Biomed Mater Res, 1998. 42(1): p. 55-65.
4. Marie, S., *International Adhesions Society*. 2000, International Adhesions Society.
5. Lai, H. S., et al., *Tissue plasminogen activator reduces intraperitoneal adhesion after intestinal resection in rats*. J Formos Med Assoc, 1998. 97(5): p. 323-7.
6. Saed, G. M. and M. P. Diamond, *Modulation of the expression of tissue plasminogen activator and its inhibitor by hypoxia in human peritoneal and adhesion fibroblasts*. Fertil Steril, 2003. 79(1): p. 164-8.
7. Hill-West, J. L., R. C. Dunn, and J. A. Hubbell, *Local release of fibrinolytic agents for adhesion prevention*. J Surg Res, 1995. 59(6): p. 759-63.
8. Chowdhury, S. M. and J. A. Hubbell, *Adhesion prevention with ancrod released via a tissue-adherent hydrogel*. J Surg Res, 1996. 61(1): p. 58-64.
9. Bertrand, J. R., et al., *Comparison of antisense oligonucleotides and siRNAs in cell culture and in vivo*. Biochem Biophys Res Commun, 2002. 296(4): p. 1000-4.
10. Elbashir, S. M., W. Lendeckel, and T. Tuschl, *RNA interference is mediated by 21- and 22-nucleotide RNAs*. Genes Dev, 2001. 15(2): p. 188-200.
11. Czauderna, F., et al., *Structural variations and stabilising modifications of synthetic siRNAs in mammalian cells*. Nucleic Acids Res, 2003. 31(11): p. 2705-16.
12. Grunweller, A., et al., *Comparison of different antisense strategies in mammalian cells using locked nucleic acids, 2'-O-methyl RNA, phosphorothioates and small interfering RNA*. Nucleic Acids Res, 2003. 31(12): p. 3185-93.
13. Simeoni, F., et al., *Insight into the mechanism of the peptide-based gene delivery system MPG: implications for delivery of siRNA into mammalian cells*. Nucleic Acids Res, 2003. 31(11): p. 2717-24.
14. Kircheis, R., et al., *Coupling of cell-binding ligands to polyethylenimine for targeted gene delivery*. Gene Ther, 1997. 4(5): p. 409-18.
15. Gottschalk, S., et al., *Folate receptor mediated DNA delivery into tumor cells: potosomal disruption results in enhanced gene expression*. Gene Ther, 1994. 1(3): p. 185-91.
16. Erbacher, P., et al., *Gene transfer by DNA/glycosylated polylysine complexes into human blood monocyte-derived macrophages*. Hum Gene Ther, 1996. 7(6): p. 721-9.
17. Blessing, T., et al., *Different strategies for formation of pegylated EGF-conjugated PEI/DNA complexes for targeted gene delivery*. Bioconjug Chem, 2001. 12(4): p. 529-37.
18. Harbottle, R. P., et al., *An RGD-oligolysine peptide: a prototype construct for integrin-mediated gene delivery*. Hum Gene Ther, 1998. 9(7): p. 1037-47.
19. Carlisle, R. C., *Use of adenovirus proteins to enhance the transfection activity of synthetic gene delivery systems*. Curr Opin Mol Ther, 2002. 4(4): p. 306-12.
20. Bell, P. C., et al., *Transfection mediated by gemini surfactants: engineered escape from the endosomal compartment*. J Am Chem Soc, 2003. 125(6): p. 1551-8.
21. Reich, S. J., et al., *Small interfering RNA (siRNA) targeting VEGF effectively inhibits ocular neovascularization in a mouse model*. Mol Vis, 2003. 9: p. 210-6.
22. Kabanov, A. V., E. V. Batrakova, and V. Y. Alakhov, *Pluronic block copolymers as novel polymer therapeutics for drug and gene delivery*. J Control Release, 2002. 82(2-3): p. 189-212.
23. Chandaroy, P., et al., *Utilizing temperature-sensitive association of Pluronic F-127 with lipid bilayers to control liposome-cell adhesion*. Biochim Biophys Acta, 2002. 1559(1): p. 32-42.
24. Zhou, D., P. Alexandridis, and A. Khan, *Self-Assembly in a Mixture of Two Poly(ethylene oxide)-b-poly(propylene oxide)-b-poly(ethylene oxide) Copolymers in Water*. J Colloid Interface Sci, 1996. 183(2): p. 339-50.

25. Discher, B. M., et al., *Polymersomes: tough vesicles made from diblock copolymers*. Science, 1999. 284 (5417): p. 1143-6.
26. Napoli, A., et al., *New synthetic methodologies for amphiphilic multiblock copolymers of ethylene glycol and propylene sulfide*. Macromolecules, 2001. 34(26): p. 8913-8917.
27. Napoli, A., et al., *Lyotropic behavior in water of amphiphilic ABA triblock copolymers based on poly(propylene sulfide) and poly(ethylene glycol)*. Langmuir, 2002. 18(22): p. 8324-8329.
28. Elbashir, S. M., et al., *Duplexes of 21-nucleotide RNAs mediate RNA interference in cultured mammalian cells*. Nature, 2001. 411(6836): p. 494-8.
29. Katayose, S. and K. Kataoka, *Water-soluble polyion complex associates of DNA and poly(ethylene glycol)-poly(L-lysine) block copolymer*. Bioconjug Chem, 1997. 8(5): p. 702-7.
30. Frankel, A and Pabo, C *Cellular uptake of the tat protein from human immunodeficiency virus*. Cell 55, 1189-1193 (1988)
31. Green, M and Loewenstein, P *Autonomous functional domains of chemically synthesized human immunodeficiency virus tat trans-activator protein*. Cell 55, 1179-1188 (1988)
32. Napoli A et al. *Oxidation-responsive polymeric vesicles*, Nature Materials, 2004. 3(3): p. 183-189.
33. East L, Isacke C M. *The mannose receptor family*. Biochimica et Biophysica Acta, 2002 1572: p. 364-386.

OTHER EMBODIMENTS

The description of the specific embodiments of the invention is presented for the purposes of illustration. It is not intended to be exhaustive nor to limit the scope of the invention to the specific forms described herein. Although the invention has been described with reference to several embodiments, it will be understood by one of ordinary skill in the art that various modifications can be made without departing from the spirit and the scope of the invention, as set forth in the claims. All patents, patent applications, and publications referenced herein are hereby incorporated by reference.

Other embodiments are within the claims.

The invention claimed is:

1. A triblock copolymer comprising:
   (i) a hydrophilic block comprising poly(ethylene glycol) (PEG), poly(ethylene oxide)-co-poly(propylene oxide) di- or multiblock copolymer, poly(ethylene oxide), poly(vinvl alcohol), poly(ethylene-co-vinyl alcohol), poly(N-vinyl pyrrolidone), poly(acrvlic acid), poly(ethyloxazoline), poly(alkylacrylates), poly(acrvlamide), poly(N-alkylacrylamides), polysaccharide, poly(N,N-dialkylacrylamides), hyaluronic acid, or poly(N-acryloylmorpholine);
   (ii) a hydrophobic block comprising a polymer selected from the group consisting of poly(propylene sulfide) (PPS), poly(propylene glycol), and esterified poly(acrylic acid); and
   (iii) a positively charged block capable of reversibly complexing a negatively charged molecule, wherein said hydrophobic block is disposed between said hydrophilic block and said positively charged block, wherein said hydrophobic block and said positively charged block are bonded to each other through a bond that is labile in an endosome.

2. The triblock copolymer of claim 1, wherein said triblock copolymer is capable of self-assembling into a supramolecular structure.

3. The triblock copolymer of claim 2, wherein said supramolecular structure is a micelle or vesicle.

4. The triblock copolymer of claim 1, wherein said bond comprises a disulfide bond, vinyl ether, orthoester, acyl hydrazone, or a —N—$PO_3$— group.

5. The triblock copolymer of claim 1, wherein said hydrophilic block comprises poly(ethylene glycol).

6. The triblock copolymer of claim 1, wherein said hydrophobic block comprises poly(propylene sulfide) or poly(propylene glycol.

7. The triblock copolymer of claim 1, wherein said positively charged block comprises a polypeptide, poly(ethyleneimine), or poly(amidoamine).

8. The triblock copolymer of claim 7, wherein said polypeptide comprises SEQ ID NO: 1, 2, 4, or 5 or an Arg-Lys copolymer.

9. The triblock copolymer of claim 1, wherein said hydrophilic block is PEG, said hydrophobic block is PPS, and said positively charged block is a polypeptide.

10. The triblock copolymer of claim 9, wherein said triblock copolymer comprises $PEG_{45}$, $PPS_5$ or $PPS_{10}$, and SEQ ID NO: 1 or SEQ ID NO: 2.

11. The triblock copolymer of claim 1, further comprising an internalization agent.

12. The triblock copolymer of claim 11, wherein said internalization agent comprises transferrin, folate, a lectin, a growth factor, an RGD peptide, or a mannose-containing glycopeptide.

13. The triblock copolymer of claim 1, further comprising a negatively charged molecule complexed to said positively charged block.

14. The triblock copolymer of claim 13, wherein said negatively charged molecule comprises a nucleic acid.

15. The triblock copolymer of claim 14, wherein said nucleic acid is an siRNA, an olioodeoxynucleotide (ODN), or a plasmid.

16. The triblock copolymer of claim 15, wherein said nucleic acid is an siRNA that targets HIF-1α or PAI-1.

17. A pharmaceutical composition comprising (i) a triblock copolymer of claim 1, (ii) a nucleic acid complexed to said triblock copolymer, and (iii) a pharmaceutically acceptable diluent.

18. A triblock copolymer comprising:
   (i) a hydrophilic block comprising poly(ethylene glycol) (PEG), poly(ethylene oxide)-co-poly(propylene oxide) di- or multiblock copolymers, poly(ethylene oxide), poly(vinvl alcohol), poly(ethylene-co-vinyl alcohol), poly(N-vinyl pyrrolidone), poly(acrylic acid), poly(ethyloxazoline), poly(alkylacrylates), poly(acrvlamide), poly(N-alkylacrylamides), polysaccharide, poly(N,N-dialkylacrylamides), hyaluronic acid, or poly(N-acryloylmorpholine);
   (ii) a hydrophobic block comprising a poly(propylene sulfide) (PPS) or poly(propylene glycol); and
   (iii) a positively charged block capable of reversibly complexing a negatively charged molecule, said positively charged block having between 5 and 20 positive charges;
   wherein said hydrophobic block is disposed between said hydrophilic block and said positively charged block.

19. The triblock copolymer of claim 18, wherein said triblock copolymer is capable of self-assembling into a supramolecular structure.

20. The triblock copolymer of claim 19, wherein said supramolecular structure is a micelle or vesicle.

21. The triblock copolymer of claim 18, wherein said hydrophobic block and said positively charged block are bonded to each other through a bond that is labile in an endosome.

22. The triblock copolymer of claim 21, wherein said bond comprises a disulfide bond, vinyl ether, orthoester, acyl hydrazone, or a —N—$PO_3$— group.

23. The triblock copolymer of claim 18, wherein said hydrophilic block comprises poly(ethylene glycol) (PEG).

24. The triblock copolymer of claim 18, wherein said hydrophobic block comprises poly(propylene sulfide).

25. The triblock copolymer of claim 18, wherein said positively charged block comprises a polypeptide, poly(ethyleneimine), or poly(amidoamine).

26. The triblock copolymer of claim 25, wherein said polypeptide comprises (SEQ ID NO: 1 2, 4, or 5 or an Arg-Lys copolymer.

27. The triblock copolymer of claim 18, wherein said hydrophilic block is PEG, said hydrophobic block is PPS, and said positively charged block is a polypeptide.

28. The triblock copolymer of claim 27, wherein said triblock copolymer comprises $PEG_{45}$, $PPS_5$ or $PPS_{10}$, and SEQ ID NO: 1 or SEQ ID NO: 2.

29. The triblock copolymer of claim 18, further comprising an internalization agent.

30. The triblock copolymer of claim 29, wherein said internalization agent comprises transferrin, folate, a lectin, a growth factor, an RGD peptide, or a mannose-containing glycopeptide.

31. The triblock copolymer of claim 18, further comprising a negatively charged molecule complexed to said positively charged block.

32. The triblock copolymer of claim 31, wherein said negatively charged molecule comprises a nucleic acid.

33. The triblock copolymer of claim 32, wherein said nucleic acid is an siRNA, an oliaodeoxynucleotide (ODN), or a plasmid.

34. The triblock copolymer of claim 33, wherein said nucleic acid is an siRNA that targets HIF-1α or PAI-1.

35. A pharmaceutical composition comprising (i) a triblock copolymer of claim 18, (ii) a nucleic acid complexed to said triblock copolymer, and (iii) a pharmaceutically acceptable diluent.

36. The triblock copolymer of claim 1, wherein said hydrophobic block is poly(propylene sulfide).

* * * * *

UNITED STATES PATENT AND TRADEMARK OFFICE
CERTIFICATE OF CORRECTION

Page 1 of 2

PATENT NO. : 9,505,867 B2
APPLICATION NO. : 11/916252
DATED : November 29, 2016
INVENTOR(S) : Tatiana Segura et al.

It is certified that error appears in the above-identified patent and that said Letters Patent is hereby corrected as shown below:

In the Specification

Column 2, Line 54, replace "infertility [2, 3], In 1994" with --infertility [2, 3]. In 1994--.

Column 3, Line 42, replace "polyethylene-co-vinyl alcohol)" with --poly(ethylene-co-vinyl alcohol)--.

Column 10, Line 49, replace "triblockcopolymers" with --triblock copolymers--.

Column 12, Line 10, replace "polypropylene glycol)" with --poly(propylene glycol)--.

Column 19, Line 34, replace "*K kingae*" with --*K. kingae*--;
    Line 35, replace "*K. oxalis,*" with --*K. oralis,*--;
    Line 36, replace "*M phenylpyruvica,*" with --*M. phenylpyruvica,*--;
    Line 37, replace "*vaginalis, Bacteroides*" with --*vaginalis, Bacteroides flagilis,*--;
    Line 41, replace "*M avium,*" with --*M. avium,*--;
        Replace "*M leprae,*" with --*M. leprae,*--;
    Line 46, replace "*C. inatruchoti,*" with --*C. matruchotii,*--.

Column 20, Lines 62-63, replace "(dd, 2H, -H2OCH2CH=CH2)," with --(dd, 2H, -CH2OCH2CH=CH2),--.

Column 21, Line 10, replace "(0.456 mL'5, 6.4 mmol×5)." with --(0.456 mL×5, 6.4 mmol×5).--.

In the Claims

Column 29, Line 23, replace "poly(vinvl alcohol)," with --polyvinyl alcohol),--;
    Line 24, replace "poly(acrvlic acid), with --poly(acrylic acid),--;
    Lines 25-26, replace "poly(acrvlamide)," with --poly(acrylamide),--;
    Line 53, replace "poly(propylene glycol." with --poly(propylene glycol).--.

Signed and Sealed this
Eleventh Day of December, 2018

Andrei Iancu
*Director of the United States Patent and Trademark Office*

CERTIFICATE OF CORRECTION (continued)
U.S. Pat. No. 9,505,867 B2

Column 30, Line 29, replace "olioodeoxynucleotide" with --oligodeoxynucleotide--;
    Line 41, replace "poly(vinvl alcohol)," with --poly(vinyl alcohol),--;
    Line 43-44, replace "poly(acrvlamide)," with --poly(acrylamide),--.

Column 31, Line 10, replace "(SEQ" with --SEQ--.

Column 32, Line 11, replace "oliaodeoxynucleotide" with --oligodeoxynucleotide--.